(12) United States Patent
Dhamija et al.

(10) Patent No.: US 12,142,385 B2
(45) Date of Patent: Nov. 12, 2024

(54) METHODS AND SYSTEMS FOR REDUCING A RISK OF SPREAD OF DISEASE AMONG PEOPLE IN A SPACE

(71) Applicant: Honeywell International Inc., Charlotte, NC (US)

(72) Inventors: Vijay Dhamija, Cumming, GA (US); Lalitha M. Eswara, Bangalore (IN); Ismaiel Shaik, Bangalore (IN); Mourian Balasubramanian, Bangalore (IN); Abhisekh Jain, Madurai (IN); Siddharth Sonkamble, Mumbai (IN); Jitendra Chaurasia, Bengaluru (IN); Manu Thomas, Pandalam (IN)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 464 days.

(21) Appl. No.: 17/328,356

(22) Filed: May 24, 2021

(65) Prior Publication Data
US 2021/0398691 A1 Dec. 23, 2021

Related U.S. Application Data

(60) Provisional application No. 63/042,414, filed on Jun. 22, 2020.

(51) Int. Cl.
*G16H 50/80* (2018.01)
*G06V 20/40* (2022.01)
(Continued)

(52) U.S. Cl.
CPC ............ *G16H 50/80* (2018.01); *G06V 20/41* (2022.01); *G06V 20/53* (2022.01); *G06V 40/20* (2022.01); *G16H 40/20* (2018.01); *G06V 20/44* (2022.01)

(58) Field of Classification Search
CPC ........ G16H 50/80; G16H 40/20; G06V 20/41; G06V 20/53; G06V 40/20; G06V 20/44
See application file for complete search history.

(56) References Cited

U.S. PATENT DOCUMENTS

| 191,512 A | 6/1877 | Bennett et al. |
| 4,009,647 A | 3/1977 | Howorth |
| (Continued) | | |

FOREIGN PATENT DOCUMENTS

| CA | 2387100 A1 | 11/2003 |
| CA | 2538139 A1 | 3/2005 |
| (Continued) | | |

OTHER PUBLICATIONS

T. Marciniak, A. Dąbrowski, A. Chmielewska and M. "Real-time bi-directional people counting using video blob analysis," 2012 Joint Conference New Trends in Audio & Video and Signal Processing: Algorithms, Architectures, Arrangements and Applications (NTAV/SPA), Lodz, Poland, 2012, pp. 161-166. (Year: 2012)*
(Continued)

*Primary Examiner* — Santiago Garcia
(74) *Attorney, Agent, or Firm* — Seager, Tufte & Wickhem, LLP

(57) ABSTRACT

Methods and systems for location tracking or maintaining a count of people in a building or space. An illustrative method may include storing a background image of a field of view of a video camera and receiving a video stream from the video camera. Background subtraction may be performed to identify one or more blobs in the field of view of the video camera. The size of the one or more blobs may be compared to an expected size of the blob at a similar distance from the camera. When the size of the blob is greater than the expected size of a person at the determined distance of the corresponding blob by more than a prede-
(Continued)

termined threshold the blob may be counted as two or more people.

10 Claims, 10 Drawing Sheets

(51) Int. Cl.
*G06V 20/52* (2022.01)
*G06V 40/20* (2022.01)
*G16H 40/20* (2018.01)

(56) References Cited

U.S. PATENT DOCUMENTS

| | | | |
|---|---|---|---|
| 4,375,637 A | 3/1983 | Desjardins |
| 4,918,615 A | 4/1990 | Suzuki et al. |
| 4,939,922 A | 7/1990 | Smalley et al. |
| 5,566,084 A | 10/1996 | Cmar |
| 5,727,579 A | 3/1998 | Chardack |
| 5,745,126 A | 4/1998 | Jain et al. |
| 5,751,916 A | 5/1998 | Kon et al. |
| 5,777,598 A | 7/1998 | Gowda et al. |
| 5,973,662 A | 10/1999 | Singers et al. |
| 6,065,842 A | 5/2000 | Fink |
| 6,139,177 A | 10/2000 | Venkatraman et al. |
| 6,144,993 A | 11/2000 | Fukunaga et al. |
| 6,157,943 A | 12/2000 | Meyer |
| 6,229,429 B1 | 5/2001 | Horon |
| 6,238,337 B1 | 5/2001 | Kambhatla et al. |
| 6,334,211 B1 | 12/2001 | Kojima et al. |
| 6,353,853 B1 | 3/2002 | Gravlin |
| 6,369,695 B2 | 4/2002 | Horon |
| 6,375,038 B1 | 4/2002 | Daansen et al. |
| 6,429,868 B1 | 8/2002 | Dehner, Jr. et al. |
| 6,473,084 B1 | 10/2002 | Phillips et al. |
| 6,487,457 B1 | 11/2002 | Hull et al. |
| 6,580,950 B1 | 6/2003 | Johnson et al. |
| 6,598,056 B1 | 7/2003 | Hull et al. |
| 6,619,555 B2 | 9/2003 | Rosen |
| 6,704,012 B1 | 3/2004 | Lefave |
| 6,720,874 B2 | 4/2004 | Fufido et al. |
| 6,741,915 B2 | 5/2004 | Poth |
| 6,796,896 B2 | 9/2004 | Laiti |
| 6,801,199 B1 | 10/2004 | Wallman |
| 6,816,878 B1 | 11/2004 | Zimmers et al. |
| 6,876,951 B2 | 4/2005 | Skidmore et al. |
| 6,882,278 B2 | 4/2005 | Winings et al. |
| 6,904,385 B1 | 6/2005 | Budike, Jr. |
| 6,907,387 B1 | 6/2005 | Reardon |
| 6,911,177 B2 | 6/2005 | Deal |
| 6,993,403 B1 | 1/2006 | Dadebo et al. |
| 6,993,417 B2 | 1/2006 | Osann, Jr. |
| 7,023,440 B1 | 4/2006 | Havekost et al. |
| 7,031,880 B1 | 4/2006 | Seem et al. |
| 7,062,722 B1 | 6/2006 | Carlin et al. |
| 7,110,843 B2 | 9/2006 | Pagnano et al. |
| 7,139,685 B2 | 11/2006 | Bascle et al. |
| 7,164,972 B2 | 1/2007 | Imhof et al. |
| 7,183,899 B2 | 2/2007 | Behnke |
| 7,200,639 B1 | 4/2007 | Yoshida |
| 7,222,111 B1 | 5/2007 | Budike, Jr. |
| 7,222,800 B2 | 5/2007 | Wruck |
| 7,257,397 B2 | 8/2007 | Shamoon et al. |
| 7,280,030 B1 | 10/2007 | Monaco |
| 7,292,908 B2 | 11/2007 | Borne et al. |
| 7,295,116 B2 | 11/2007 | Kumar et al. |
| 7,302,313 B2 | 11/2007 | Sharp et al. |
| 7,308,323 B2 | 12/2007 | Kruk et al. |
| 7,308,388 B2 | 12/2007 | Beverina et al. |
| 7,313,447 B2 | 12/2007 | Hsiung et al. |
| 7,346,433 B2 | 3/2008 | Budike, Jr. |
| 7,356,548 B1 | 4/2008 | Culp et al. |
| 7,379,782 B1 | 5/2008 | Cocco |
| 7,383,148 B2 | 6/2008 | Ahmed |
| 7,434,742 B2 | 10/2008 | Mueller et al. |
| 7,447,333 B1 | 11/2008 | Masticola et al. |
| 7,466,224 B2 | 12/2008 | Ward et al. |
| 7,496,472 B2 | 2/2009 | Seem |
| 7,512,450 B2 | 3/2009 | Ahmed |
| 7,516,490 B2 | 4/2009 | Riordan et al. |
| 7,548,833 B2 | 6/2009 | Ahmed |
| 7,551,092 B1 | 6/2009 | Henry |
| 7,557,729 B2 | 7/2009 | Hubbard et al. |
| 7,567,844 B2 | 7/2009 | Thomas et al. |
| 7,596,473 B2 | 9/2009 | Hansen et al. |
| 7,610,910 B2 | 11/2009 | Ahmed |
| 7,626,507 B2 | 12/2009 | LaCasse |
| 7,664,574 B2 | 2/2010 | Imhof et al. |
| 7,682,464 B2 | 3/2010 | Glenn et al. |
| 7,702,421 B2 | 4/2010 | Sullivan et al. |
| 7,729,882 B2 | 6/2010 | Seem |
| 7,755,494 B2 | 7/2010 | Melker et al. |
| 7,761,310 B2 | 7/2010 | Rodgers |
| 7,774,227 B2 | 8/2010 | Srivastava |
| 7,797,188 B2 | 9/2010 | Srivastava |
| 7,819,136 B1 | 10/2010 | Eddy |
| 7,822,806 B2 | 10/2010 | Frank et al. |
| 7,856,370 B2 | 12/2010 | Katta et al. |
| 7,978,083 B2 | 7/2011 | Melker et al. |
| 7,984,384 B2 | 7/2011 | Chaudhri et al. |
| 7,986,323 B2 | 7/2011 | Kobayashi et al. |
| 8,024,666 B2 | 9/2011 | Thompson |
| 8,086,047 B2 | 12/2011 | Penke et al. |
| 8,099,178 B2 | 1/2012 | Mairs et al. |
| 8,151,280 B2 | 4/2012 | Sather et al. |
| 8,176,095 B2 | 5/2012 | Murray et al. |
| 8,218,871 B2 | 7/2012 | Angell et al. |
| 8,219,660 B2 | 7/2012 | McCoy et al. |
| 8,271,941 B2 | 9/2012 | Zhang et al. |
| 8,294,585 B2 | 10/2012 | Barnhill |
| 8,302,020 B2 | 10/2012 | Louch et al. |
| 8,320,634 B2 | 11/2012 | Deutsch |
| 8,334,422 B2 | 12/2012 | Gutsol et al. |
| 8,344,893 B1 | 1/2013 | Drammeh |
| 8,375,118 B2 | 2/2013 | Hao et al. |
| 8,476,590 B2 | 7/2013 | Stratmann et al. |
| 8,516,016 B2 | 8/2013 | Park et al. |
| 8,558,660 B2 | 10/2013 | Nix et al. |
| 8,639,527 B2 | 1/2014 | Rensvold et al. |
| 8,698,637 B2 | 4/2014 | Raichman |
| 8,816,860 B2 | 8/2014 | Ophardt et al. |
| 8,869,027 B2 | 10/2014 | Louch et al. |
| 8,904,497 B2 | 12/2014 | Hsieh |
| 8,936,944 B2 | 1/2015 | Peltz et al. |
| 8,947,437 B2 | 2/2015 | Garr et al. |
| 8,950,019 B2 | 2/2015 | Loberger et al. |
| 9,000,926 B2 | 4/2015 | Hollock et al. |
| 9,030,325 B2 | 5/2015 | Taneff |
| 9,098,738 B2 | 8/2015 | Bilet et al. |
| 9,105,071 B2 | 8/2015 | Fletcher et al. |
| 9,175,356 B2 | 11/2015 | Peltz et al. |
| 9,240,111 B2 | 1/2016 | Scott et al. |
| 9,280,884 B1 | 3/2016 | Schultz et al. |
| 9,292,972 B2 | 3/2016 | Hailemariam et al. |
| 9,320,662 B2 | 4/2016 | Hayes et al. |
| 9,370,600 B1 | 6/2016 | DuPuis et al. |
| 9,373,242 B1 | 6/2016 | Conrad et al. |
| 9,396,638 B2 | 7/2016 | Wildman et al. |
| 9,311,807 B2 | 8/2016 | Schultz et al. |
| 9,406,212 B2 | 8/2016 | De Luca et al. |
| 9,418,535 B1 | 8/2016 | Felch et al. |
| 9,418,536 B1 | 8/2016 | Felch et al. |
| 9,449,219 B2 | 9/2016 | Bilet et al. |
| 9,477,543 B2 | 10/2016 | Henley et al. |
| 9,497,832 B2 | 11/2016 | Verberkt et al. |
| 9,513,364 B2 | 12/2016 | Hall et al. |
| 9,526,380 B2 | 12/2016 | Hamilton et al. |
| 9,526,806 B2 | 12/2016 | Park et al. |
| 9,536,415 B2 | 1/2017 | De Luca et al. |
| 9,558,648 B2 | 1/2017 | Douglas |
| 9,591,267 B2 | 3/2017 | Lipton et al. |
| 9,613,518 B2 | 4/2017 | Dunn et al. |
| 9,618,224 B2 | 4/2017 | Emmons et al. |
| 9,640,059 B2 | 5/2017 | Hyland |

(56) References Cited

U.S. PATENT DOCUMENTS

| | | |
|---|---|---|
| 9,672,360 B2 | 6/2017 | Barkan |
| 9,710,700 B2 | 7/2017 | Bilet et al. |
| 9,715,242 B2 | 7/2017 | Pillai et al. |
| 9,721,452 B2 | 8/2017 | Felch et al. |
| 9,729,945 B2 | 8/2017 | Schultz et al. |
| 9,784,464 B2 | 10/2017 | Yamamoto et al. |
| 9,843,743 B2 | 12/2017 | Lewis et al. |
| 9,856,634 B2 | 1/2018 | Rodenbeck et al. |
| 9,872,088 B2 | 1/2018 | Fadell et al. |
| 9,875,639 B2 | 1/2018 | Bone et al. |
| 9,911,312 B2 | 3/2018 | Wildman et al. |
| 9,940,819 B2 | 4/2018 | Ferniany |
| 9,956,306 B2 | 5/2018 | Brais et al. |
| 9,986,175 B2 | 5/2018 | Frank et al. |
| 10,009,579 B2 * | 6/2018 | Wang .................... G06V 20/64 |
| 10,087,608 B2 | 10/2018 | Dobizl et al. |
| 10,223,894 B2 | 3/2019 | Raichman |
| 10,228,837 B2 | 3/2019 | Hua et al. |
| 10,235,865 B2 | 3/2019 | Thyroff |
| 10,251,610 B2 | 4/2019 | Parthasarathy et al. |
| 10,303,843 B2 | 5/2019 | Bitran et al. |
| 10,332,382 B2 | 6/2019 | Thyroff |
| 10,514,817 B2 | 12/2019 | Hua et al. |
| 10,565,844 B2 | 2/2020 | Pourmohammad et al. |
| 10,602,474 B2 | 3/2020 | Goldstein |
| 10,607,147 B2 | 3/2020 | Raykov et al. |
| 10,915,760 B1 * | 2/2021 | Lee ........................ G06V 20/53 |
| 2002/0111698 A1 | 8/2002 | Graziano et al. |
| 2002/0130868 A1 | 9/2002 | Smith |
| 2003/0028269 A1 | 2/2003 | Spriggs et al. |
| 2003/0030637 A1 | 2/2003 | Grinstein et al. |
| 2003/0046862 A1 | 3/2003 | Wolf et al. |
| 2003/0071814 A1 | 4/2003 | Jou et al. |
| 2003/0078677 A1 | 4/2003 | Hull et al. |
| 2003/0083957 A1 | 5/2003 | Olefson |
| 2003/0103075 A1 | 6/2003 | Rosselot |
| 2003/0171851 A1 | 9/2003 | Brickfield et al. |
| 2003/0214400 A1 | 11/2003 | Mizutani et al. |
| 2003/0233432 A1 | 12/2003 | Davis et al. |
| 2004/0001009 A1 | 1/2004 | Winings et al. |
| 2004/0064260 A1 | 4/2004 | Padmanabhan et al. |
| 2004/0130620 A1 * | 7/2004 | Buehler ................. G06V 40/20 348/E7.086 |
| 2004/0143474 A1 | 7/2004 | Haeberle et al. |
| 2004/0153437 A1 | 8/2004 | Buchan |
| 2004/0168115 A1 | 8/2004 | Bauernschmidt et al. |
| 2004/0233192 A1 | 11/2004 | Hopper |
| 2004/0260411 A1 | 12/2004 | Cannon |
| 2005/0010460 A1 | 1/2005 | Mizoguchi et al. |
| 2005/0119767 A1 | 6/2005 | Kiwimagi et al. |
| 2005/0143863 A1 | 6/2005 | Ruane et al. |
| 2005/0267900 A1 | 12/2005 | Ahmed et al. |
| 2006/0004841 A1 | 1/2006 | Heikkonen et al. |
| 2006/0009862 A1 | 1/2006 | Imhof et al. |
| 2006/0017547 A1 | 1/2006 | Buckingham et al. |
| 2006/0020177 A1 | 1/2006 | Seo et al. |
| 2006/0028471 A1 | 2/2006 | Kincaid et al. |
| 2006/0029256 A1 | 2/2006 | Miyoshi et al. |
| 2006/0058900 A1 | 3/2006 | Johanson et al. |
| 2006/0062429 A1 * | 3/2006 | Ramaswamy ........ G06T 7/254 725/12 |
| 2006/0067545 A1 | 3/2006 | Lewis et al. |
| 2006/0067546 A1 | 3/2006 | Lewis et al. |
| 2006/0077255 A1 | 4/2006 | Cheng |
| 2006/0184326 A1 | 8/2006 | McNally et al. |
| 2006/0231568 A1 | 10/2006 | Lynn et al. |
| 2006/0265664 A1 | 11/2006 | Simons et al. |
| 2006/0279630 A1 | 12/2006 | Aggarwal et al. |
| 2007/0016955 A1 | 1/2007 | Goldberg et al. |
| 2007/0055757 A1 | 3/2007 | Mairs et al. |
| 2007/0055760 A1 | 3/2007 | McCoy et al. |
| 2007/0061046 A1 | 3/2007 | Mairs et al. |
| 2007/0067062 A1 | 3/2007 | Mairs et al. |
| 2007/0088534 A1 | 4/2007 | MacArthur et al. |
| 2007/0090951 A1 | 4/2007 | Chan et al. |
| 2007/0091091 A1 | 4/2007 | Gardiner et al. |
| 2007/0101433 A1 | 5/2007 | Louch et al. |
| 2007/0114295 A1 | 5/2007 | Jenkins |
| 2007/0120652 A1 | 5/2007 | Behnke |
| 2007/0139208 A1 | 6/2007 | Kates |
| 2007/0216682 A1 | 9/2007 | Navratil et al. |
| 2007/0219645 A1 | 9/2007 | Thomas et al. |
| 2007/0239484 A1 | 10/2007 | Arond et al. |
| 2007/0268122 A1 | 11/2007 | Kow et al. |
| 2008/0001763 A1 | 1/2008 | Raja et al. |
| 2008/0027885 A1 | 1/2008 | Van Putten et al. |
| 2008/0036593 A1 | 2/2008 | Rose-Pehrsson et al. |
| 2008/0062167 A1 | 3/2008 | Boggs et al. |
| 2008/0099045 A1 | 5/2008 | Glenn et al. |
| 2008/0103798 A1 | 5/2008 | Domenikos et al. |
| 2008/0120396 A1 | 5/2008 | Jayaram et al. |
| 2008/0144885 A1 | 6/2008 | Zucherman et al. |
| 2008/0183424 A1 | 7/2008 | Seem |
| 2008/0194009 A1 | 8/2008 | Marentis |
| 2008/0198231 A1 | 8/2008 | Ozdemir et al. |
| 2008/0209342 A1 | 8/2008 | Taylor et al. |
| 2008/0222565 A1 | 9/2008 | Taylor et al. |
| 2008/0224862 A1 | 9/2008 | Cirker |
| 2008/0242945 A1 | 10/2008 | Gugliotti et al. |
| 2008/0250800 A1 | 10/2008 | Wetzel |
| 2008/0279420 A1 | 11/2008 | Masticola et al. |
| 2008/0280275 A1 | 11/2008 | Collopy |
| 2008/0303658 A1 | 12/2008 | Melker et al. |
| 2008/0306985 A1 | 12/2008 | Murray et al. |
| 2008/0320552 A1 | 12/2008 | Kumar et al. |
| 2009/0001181 A1 | 1/2009 | Siddaramanna et al. |
| 2009/0024944 A1 | 1/2009 | Louch et al. |
| 2009/0065596 A1 | 3/2009 | Seem et al. |
| 2009/0083120 A1 | 3/2009 | Strichman et al. |
| 2009/0096791 A1 | 4/2009 | Abshear et al. |
| 2009/0125337 A1 | 5/2009 | Abri |
| 2009/0125825 A1 | 5/2009 | Rye et al. |
| 2009/0144023 A1 | 6/2009 | Seem |
| 2009/0157744 A1 | 6/2009 | McConnell |
| 2009/0160673 A1 | 6/2009 | Cirker |
| 2009/0322782 A1 | 12/2009 | Kimchi et al. |
| 2010/0027875 A1 * | 2/2010 | Hampapur ........... G06V 40/103 382/159 |
| 2010/0048167 A1 | 2/2010 | Chow et al. |
| 2010/0058248 A1 | 3/2010 | Park |
| 2010/0064001 A1 | 3/2010 | Daily |
| 2010/0070089 A1 | 3/2010 | Harrod et al. |
| 2010/0073162 A1 | 3/2010 | Johnson et al. |
| 2010/0123560 A1 | 5/2010 | Nix et al. |
| 2010/0134296 A1 | 6/2010 | Hwang |
| 2010/0156628 A1 | 6/2010 | Ainsbury et al. |
| 2010/0156630 A1 | 6/2010 | Ainsbury |
| 2010/0188228 A1 | 7/2010 | Hyland |
| 2010/0195865 A1 * | 8/2010 | Luff ..................... G06V 10/421 382/100 |
| 2010/0223198 A1 | 9/2010 | Noureldin et al. |
| 2010/0249955 A1 | 9/2010 | Sitton |
| 2010/0286937 A1 | 11/2010 | Hedley et al. |
| 2010/0318200 A1 | 12/2010 | Foslien et al. |
| 2010/0322516 A1 * | 12/2010 | Xu ........................ G06V 20/53 382/173 |
| 2010/0324962 A1 | 12/2010 | Nesler et al. |
| 2011/0010654 A1 | 1/2011 | Raymond et al. |
| 2011/0057799 A1 | 3/2011 | Taneff |
| 2011/0077779 A1 | 3/2011 | Fuller et al. |
| 2011/0083094 A1 | 4/2011 | Laycock et al. |
| 2011/0087988 A1 | 4/2011 | Ray et al. |
| 2011/0112854 A1 | 5/2011 | Koch et al. |
| 2011/0126111 A1 | 5/2011 | Gill et al. |
| 2011/0154426 A1 | 6/2011 | Doser et al. |
| 2011/0161124 A1 | 6/2011 | Lappinga et al. |
| 2011/0169646 A1 | 7/2011 | Raichman |
| 2011/0184563 A1 | 7/2011 | Foslien et al. |
| 2011/0202467 A1 | 8/2011 | Hilber et al. |
| 2011/0273298 A1 | 11/2011 | Snodgrass et al. |
| 2011/0291841 A1 | 12/2011 | Hollock et al. |
| 2011/0298301 A1 | 12/2011 | Wong et al. |
| 2011/0316703 A1 | 12/2011 | Butler et al. |
| 2011/0320054 A1 | 12/2011 | Brzezowski |

(56) References Cited

U.S. PATENT DOCUMENTS

| | | |
|---|---|---|
| 2012/0022700 A1 | 1/2012 | Drees et al. |
| 2012/0027299 A1* | 2/2012 | Ran .................... G06V 20/53 |
| | | 382/173 |
| 2012/0039503 A1 | 2/2012 | Chen et al. |
| 2012/0062382 A1 | 3/2012 | Taneff |
| 2012/0075464 A1 | 3/2012 | Derenne et al. |
| 2012/0109988 A1 | 5/2012 | Li et al. |
| 2012/0112883 A1 | 5/2012 | Wallace et al. |
| 2012/0131217 A1 | 5/2012 | Delorme et al. |
| 2012/0158185 A1 | 6/2012 | El-Mankabady et al. |
| 2012/0162435 A1* | 6/2012 | Elangovan ............ H04N 7/181 |
| | | 348/157 |
| 2012/0216243 A1 | 8/2012 | Gill et al. |
| 2012/0224057 A1 | 9/2012 | Gill et al. |
| 2012/0259466 A1 | 10/2012 | Ray et al. |
| 2012/0262472 A1 | 10/2012 | Garr et al. |
| 2012/0272146 A1 | 10/2012 | D'souza et al. |
| 2012/0291068 A1 | 11/2012 | Khushoo et al. |
| 2012/0303652 A1 | 11/2012 | Tseng |
| 2012/0310418 A1 | 12/2012 | Harrod et al. |
| 2013/0055132 A1 | 2/2013 | Foslien |
| 2013/0060794 A1 | 3/2013 | Puttabasappa et al. |
| 2013/0082842 A1 | 4/2013 | Balazs et al. |
| 2013/0086152 A1 | 4/2013 | Hersche et al. |
| 2013/0091631 A1 | 4/2013 | Hayes et al. |
| 2013/0110295 A1 | 5/2013 | Zheng et al. |
| 2013/0156273 A1* | 6/2013 | Nielsen .................... H04N 5/33 |
| | | 348/E9.053 |
| 2013/0169681 A1 | 7/2013 | Rasane et al. |
| 2013/0182904 A1* | 7/2013 | Zhang .................. G06V 40/103 |
| | | 382/103 |
| 2013/0182905 A1* | 7/2013 | Myers .................... A61B 5/1113 |
| | | 382/103 |
| 2013/0184880 A1 | 7/2013 | McMahon |
| 2013/0187775 A1 | 7/2013 | Marsden et al. |
| 2013/0204570 A1 | 8/2013 | Mendelson et al. |
| 2013/0229276 A1 | 9/2013 | Hunter |
| 2013/0268293 A1 | 10/2013 | Knudson et al. |
| 2013/0289774 A1 | 10/2013 | Day et al. |
| 2014/0032157 A1 | 1/2014 | Khiani |
| 2014/0040998 A1 | 2/2014 | Hsieh |
| 2014/0046490 A1 | 2/2014 | Foslien et al. |
| 2014/0046722 A1 | 2/2014 | Rosenbloom et al. |
| 2014/0058539 A1 | 2/2014 | Park |
| 2014/0167917 A2 | 6/2014 | Wallace et al. |
| 2014/0207291 A1 | 7/2014 | Golden et al. |
| 2014/0292518 A1 | 10/2014 | Wildman et al. |
| 2014/0307076 A1 | 10/2014 | Deutsch |
| 2014/0309757 A1 | 10/2014 | Le Sant et al. |
| 2014/0316582 A1 | 10/2014 | Berg-Sonne et al. |
| 2014/0320289 A1 | 10/2014 | Raichman |
| 2014/0342724 A1 | 11/2014 | Hill et al. |
| 2014/0355829 A1* | 12/2014 | Heu |
| 2015/0025329 A1 | 1/2015 | Amarasingham et al. |
| 2015/0032264 A1 | 1/2015 | Emmons et al. |
| 2015/0056909 A1 | 2/2015 | Chien |
| 2015/0070174 A1 | 3/2015 | Douglas |
| 2015/0077258 A1 | 3/2015 | Nelson et al. |
| 2015/0113462 A1 | 4/2015 | Chen et al. |
| 2015/0153918 A1 | 6/2015 | Chen et al. |
| 2015/0161874 A1 | 6/2015 | Thyroff et al. |
| 2015/0167995 A1 | 6/2015 | Fadell et al. |
| 2015/0168949 A1 | 6/2015 | Hua et al. |
| 2015/0194043 A1 | 7/2015 | Dunn et al. |
| 2015/0198707 A1 | 7/2015 | Al-Alusi |
| 2015/0212717 A1 | 7/2015 | Nair et al. |
| 2015/0213222 A1 | 7/2015 | Amarasingham et al. |
| 2015/0213379 A1 | 7/2015 | Nair et al. |
| 2015/0216369 A1 | 8/2015 | Hamilton et al. |
| 2015/0253748 A1 | 9/2015 | Brun et al. |
| 2015/0281287 A1 | 10/2015 | Gill et al. |
| 2016/0061476 A1 | 3/2016 | Schultz et al. |
| 2016/0061477 A1 | 3/2016 | Schultz et al. |
| 2016/0061794 A1 | 3/2016 | Schultz et al. |
| 2016/0061795 A1 | 3/2016 | Schultz et al. |
| 2016/0063833 A1 | 3/2016 | Schultz et al. |
| 2016/0066067 A1 | 3/2016 | Schultz et al. |
| 2016/0116181 A1 | 4/2016 | Aultman et al. |
| 2016/0139067 A1 | 5/2016 | Grace |
| 2016/0253897 A1 | 9/2016 | Wildman et al. |
| 2016/0255516 A1 | 9/2016 | Hill et al. |
| 2016/0298864 A1 | 10/2016 | Ekolind et al. |
| 2016/0306934 A1 | 10/2016 | Sperry et al. |
| 2016/0314683 A1 | 10/2016 | Felch et al. |
| 2016/0328948 A1 | 11/2016 | Ferniany |
| 2016/0335731 A1 | 11/2016 | Hall |
| 2016/0367925 A1 | 12/2016 | Blackley |
| 2017/0024986 A1 | 1/2017 | Austin |
| 2017/0193792 A1 | 7/2017 | Bermudez Rodriguez et al. |
| 2017/0256155 A1 | 9/2017 | Sengstaken, Jr. |
| 2017/0280949 A1 | 10/2017 | Wildman et al. |
| 2017/0294106 A1 | 10/2017 | Thyroff |
| 2017/0365024 A1 | 12/2017 | Koch et al. |
| 2018/0016773 A1 | 1/2018 | Chandler et al. |
| 2018/0151054 A1 | 5/2018 | Pi |
| 2018/0218591 A1 | 8/2018 | Easter |
| 2018/0293038 A1 | 10/2018 | Meruva et al. |
| 2018/0301014 A1 | 10/2018 | Worral et al. |
| 2018/0307913 A1* | 10/2018 | Finn .................... G06V 20/53 |
| 2018/0313695 A1 | 11/2018 | Shim et al. |
| 2018/0365957 A1 | 12/2018 | Wright et al. |
| 2019/0051138 A1 | 2/2019 | Easter |
| 2019/0139395 A1 | 5/2019 | Rogachev et al. |
| 2019/0209719 A1 | 7/2019 | Andersen et al. |
| 2020/0009280 A1 | 1/2020 | Kupa et al. |
| 2020/0012923 A1* | 1/2020 | Ghosh .................... G06N 3/047 |
| 2020/0042834 A1* | 2/2020 | Distler ................ G06V 20/653 |
| 2020/0074836 A1 | 3/2020 | Kolavennu et al. |
| 2020/0090089 A1 | 3/2020 | Aston et al. |
| 2020/0146557 A1 | 5/2020 | Cheung et al. |
| 2020/0200420 A1 | 6/2020 | Nayak et al. |
| 2020/0258364 A1* | 8/2020 | Quilici .................... H04N 5/33 |
| 2021/0374394 A1* | 12/2021 | Livoti .................... H04N 23/23 |

FOREIGN PATENT DOCUMENTS

| | | |
|---|---|---|
| CN | 103110410 A | 5/2013 |
| CN | 103970977 A | 8/2014 |
| CN | 105116848 A | 12/2015 |
| CN | 108961714 A | 12/2018 |
| CN | 110009245 A | 7/2019 |
| CN | 110084928 A | 8/2019 |
| CN | 110827457 A | 2/2020 |
| EP | 1669912 A1 | 6/2006 |
| EP | 2310981 A1 | 4/2011 |
| JP | 7085166 A | 3/1995 |
| JP | 11024735 A | 1/1999 |
| JP | 11317936 A | 11/1999 |
| JP | 2001356813 A | 12/2001 |
| JP | 2005242531 A | 9/2005 |
| JP | 2005311563 A | 11/2005 |
| KR | 1172747 B1 | 8/2012 |
| KR | 101445367 B1 | 10/2014 |
| KR | 1499081 B1 | 3/2015 |
| WO | 9621264 A3 | 11/1996 |
| WO | 2004029518 A1 | 4/2004 |
| WO | 2005045715 A2 | 5/2005 |
| WO | 2008152433 A1 | 12/2008 |
| WO | 2008157755 A1 | 12/2008 |
| WO | 2009012319 A2 | 1/2009 |
| WO | 2009079648 A1 | 6/2009 |
| WO | 2010106474 A1 | 9/2010 |
| WO | 2011025085 A1 | 3/2011 |
| WO | 2011043732 A1 | 4/2011 |
| WO | 2011057173 A2 | 5/2011 |
| WO | 2011123743 A1 | 10/2011 |
| WO | 2013062725 A1 | 5/2013 |
| WO | 2013178819 A1 | 12/2013 |
| WO | 2014009291 A1 | 1/2014 |
| WO | 2014098861 A1 | 6/2014 |
| WO | 2014135517 A1 | 9/2014 |
| WO | 2016123536 A1 | 8/2016 |

(56) References Cited

FOREIGN PATENT DOCUMENTS

| | | |
|---|---|---|
| WO | 2017057274 A1 | 4/2017 |
| WO | 2019046580 A1 | 3/2019 |
| WO | 2020024553 A1 | 2/2020 |

OTHER PUBLICATIONS

M. Ahmad, I. Ahmed and A. Adnan, "Overhead View Person Detection Using YOLO," 2019 IEEE 10th Annual Ubiquitous Computing, Electronics & Mobile Communication Conference (UEMCON), New York, NY, USA, 2019, pp. 0627-0633, doi: 10.1109/UEMCON47517.20198992980. (Year: 2019)*
Olken et al., "Object Lessons Learned from a Distributed System for Remote Building Monitoring and Operation," ACM SIGPLAN Notices, vol. 33, No. 10, pp. 284-295, Oct. 1998.
Proliphix, Inc., "Proliphix IP Devices: HTTP API," 28 pages, Jan. 23, 2006.
Proliphix, Inc., "Remote Management User Guide," 12 pages, prior to Aug. 27, 2007.
Rogan et al., "Smart and Final Food Stores: A Case Study in Web Based Energy Information and Collection," Web Based Energy Information and Control Systems: Case Studies and Application, Chapter 6, p. 59-64, 2005.
Sharp, "Actius AL3DU 3D LC Display High Performance 3D Visualization," 2 pages, prior to Mar. 17, 2006.
So et al., "Building Automation on the Information Superhighway," ASHRAE Transactions, vol. 104, Part 2, pp. 176-191, 1998.
So et al., "Building Automation Systems on the Internet," Facilities vol. 15, No. 5/6, pp. 125-133, May/Jun. 1997.
Talon, "Raptor Controller," 6 pages, Oct. 2003.
Talon, "Workstation Software," 4 pages, Nov. 2002.
Trane, "System Programming, Tracer Summit Version 14, BMTW-SVP01D-EN," 623 pages, 2002.
Lucid Design Group, Inc., "Building Dashboard," 2 pages, Printed May 30, 2013.
"America's Largest Managed Security Services Provider Launches Comprehensive, Integrated Covid-19 Safety Program for Office Buildings and Suites," KastleSafeSpaces, 5 pages, May 11, 2020.
"Biometric Door Reader With Body Temperature Detection," Kintronics, 9 pages, accessed May 21, 2020.
"Body Surface Temperature Screening with Alarm Function TVS-200IS/TVS-500IS," Nippon Avionics Co., 3 pages, accessed May 21, 2020.
"BriefCam announces video analytics innovation for contact tracing, physical distancing, occupancy management and face mask detection," BriefCam LTD, 11 pages, Jun. 5, 2020.
"Thermal Imaging SmartPhone Can be used for Temperature Screening of People," CAT, 3 pages, accessed Jul. 13, 2020.
"Contact Tracing Now Available on Identiv's Hirsch Velocity Access Control Platform," IDENTIV, 5 pages, May 21, 2020.
Silva et al., "Cough localization for the detection of respiratory diseases in pig houses," ScienceDirect, 7 pages, May 28, 2008.
Dey et al., "Evaluation of Isolation Compliance Using Real Time Video in Critical Care," North Shore University Hospital, 1 page, Oct. 9, 2015.
"Facial Attendace System With Temperature Screening Now in India," IANS, 5 pages, Mar. 19, 2020.
"Plan to Re-Open," EHIGH, 16 pages, accessed Jun. 13, 2020.
"How Smarter AI-Powered Cameras Can Mitigate the Spread of Wuhan Novel," AnyConnect, 22 pages, 2020.
"How to fight COVID-19 with machine learning," DataRevenue, 20 pages, accessed May 25, 2020.
Honeywell, "INNCONTROL 5," 2 pages, Aug. 8, 2018.
"IP Door Access Control," KINTRONICS, 21 pages, 2014.
"Kogniz AI Health Response Platform," KOGNIZ, 9 pages, accessed May 21, 2020.
"Machine Learning Could Check If You're Social Distancing Properly at Work," MIT Technology Review, 7 pages, Apr. 17, 2020.
Punn et al., "Monitoring COVID-19 social distancing with person detection and tracking via fine-tuned YOLO v3 and Deepsort techniques," 10 pages, May 6, 2020.
Burt, "NEC launches dual face biometric and fever detection system for access control," BIOMETRIC Update, 4 pages, May 8, 2020.
"Remote temperature monitoring," AXIS Communication, 10 pages, 2014.
"FebriEye—AI Based Thermal Temperature Screening System," vehant, 1 page, 2020.
"See The World in a New Way Hikvision Thermal Cameras," HIKVISION, 12 pages, 2017.
Allain, "Trying out the iPhone Infrared Camera: The FLIR One," WIRED, 15 pages, 2014.
Dasgupta, "Your voice may be able to tell you if you have Covid," Hindustan Times, 4 pages, Apr. 16, 2020.
Ganguty, "Gurugram-based startup Staqu has modified AI-powered JARVIS to battle coronavirus," YOURSTORY, 7 pages, Mar. 31, 2020.
Trane, "Creating Input/Output Objects," 196 pages, retrieved Jul. 10, 2020.
Trane, "Using the Graphing Control Editor," 181 pages, retrieved Jul. 10, 2020.
Bocicor et al. "Wireless Sensor Network based System for the Prevention of Hospital Acquired Infections", arxiv.org, Cornell University Ithaca, NY 14853, May 2, 2017, XP080947042, (Abstract).
Shhedi et al., "Traditional and ICT Solutions for Preventing the Hospital Acquired Infection", 2015 20th International Conference on Control Systems and Computer Science, IEEE, May 27, 2015, pp. 867-873, XP033188038.
Extended European Search Report, EP application No. 20151295.1, pp. 13, May 26, 2020.
U.S. Appl. No. 14/109,496, filed Dec. 17, 2013.
"What is the GE Nucleus Home Manager? How can a Home Manager Help with Energy Conservation?" GE Nucleus, 2 pages, printed Jan. 15, 2013. www.geappliances.com/home-energy-manager/about-energy-monitors.htm.
"Lucid Design Group—Building Dashboard Network—Apps," 7 pages, Jan. 15, 2013. www.luciddesigngroup.com/network/apps.php#homepage.
Preuveneers et al., "Intelligent Widgets for Intuitive Interaction and Coordination in Smart Home Environments," IEEE Eighth International Conference on Intelligent Environments, pp. 157-164, 2012.
Wu et al., "A Web 2.0 Based Scientific Application Framework," 7 pages, prior to Jul. 24, 2014.
"The Home Dashboard," CRBM info@hand website, 46 pages, prior to Apr. 25, 2013.
"Free Facilities Dashboards," eSight Energy Website, 2 pages, prior to Apr. 25, 2013.
Alerton Building Controls, Gallery Prints, 7 pages, Dec. 19, 2013.
Carter, "Industrial Energy Management Dashboards Require a Toolkit," Cross Automation, 11 pages, Nov. 4, 2013.
U.S. Appl. No. 14/169,071, filed Jan. 30, 2014.
U.S. Appl. No. 14/169,083, filed Jan. 30, 2014.
U.S. Appl. No. 14/461,188, filed Aug. 15, 2014.
U.S. Appl. No. 14/482,607, filed Sep. 10, 2014.
E-homecontrols.com, "e-Home Controls Website," link to actual website no longer works, 1 page, prior to Dec. 19, 2013.
"C&C (/)—Omniboard," 5 pages, Dec. 19, 2013. http://www.ccbac.com.
"DomController Home Automation Software—Control Anything from Anywhere," 11 pages, printed Jan. 6, 2015. http://www.domcontroller.com/en/.
"Novar OPUS BAS," 1 page, prior to Feb. 13, 2013. http://www.novar.com/ems-bas/opus-building-automation-system.
"A 3D Interactive Environment for Automated Building Control," Master's Dissertation, Instituto Superior Tecnico, 120 pages, Nov. 2012.
Panduit Corp., "Enable a Building Automation with Panduit Enterprise Solutions," 4 pages, Nov. 2012.
Honeywell, "WEBs-AX Web-Enabled Building Solutions," sales brochure, Honeywell International Inc., Mar. 2009.

(56) References Cited

OTHER PUBLICATIONS

Honeywell, "Attune Advisory Services," press release, Honeywell International Inc., Mar. 20, 2012.
EnteliWEB Overview, web pages retrieved on May 9, 2013 from http://deltacontrols.com/products/facilities-management/supervisory-software et seq. by the Internet Archive at web.archive.org.
"BACnet Protocol Implementation Conformance Statement" for enteliWEB, Delta Controls, Jul. 17, 2013.
Castle, "7 Software Platforms that Make Building Energy Management Easy," http://greentechadvocates.com/2012/11/28/7-software-platforms-that-make-building-energy-managment-easy/, Nov. 28, 2012.
EnteliWEB "Software: Enterprise Energy Management", catalog sheet, Delta Controls, 2012.
EnteliWEB "Software: Enterprise Energy Management", catalog sheet, Delta Controls, 2010.
"Intelligent Building Management Systems in Miami," Advanced Control Corp., Mar. 7, 2013.
"The Ohio State University," BACnet International Journal, vol. 5, p. 4, Jan. 2013.
Bobker et al., "Operational Effectiveness in Use of BAS," Proceedings of the 13th International Conference for Enhanced Building Operations, Oct. 8, 2013.
Castelo, "A 3D Interactive Environment for Automated Building Control," Elsevier, Nov. 8, 2012.
"Creston Special Report: How Intelligent building management solutions are reducing operational costs," Creston, 2012.
"Building Automation Software Solutions," Iconics, 2013.
Lacey, "The Top 10 Software Vendors Connecting Smart Buildings to the Smart Grid," http://www.greentechmedia.com/articles/read/the-top-10-companies-in-enterprise-smart-grid, Jul. 18, 2013.
"NiagraAX Product Model Overview," Tridium, Inc., 2005.
"An Overview of NiagraAX: A comprehensive software platform designed to create smart device applications," Tridium, Inc., 2005.
"Phoenix Controls Portal," Phoenix Controls, Inc., 2013.
Quirk, "A Brief History of BIM," Arch Daily, Dec. 7, 2012.
Samad et al., "Leveraging the Web: A Universal Framework for Building Automation," Proceedings of the 2007 American Control Conference, Jul. 11, 2007.
Sinha et al., "9 Key attributes of energy dashboards and analytics tools," Aug. 28, 2013, https://www.greenbiz.com/blog/2013/08/28/9-key-attributes-energy-dashboards-and=analytics-tools.
Sinopoli, "Dashboards for Buildings," http://www/automatedbuildings.com/news/dec10/articles/sinopoli/101119034404sinopoli.html, Dec. 2010.
Sinopoli, "Modeling Building Automation and Control Systems," http://www.automatedbuildings.com/news/jun13/articles/sinopoli/130521122303sinopoli.html, Jun. 2013.
Zito, "What is Tridium Part 1," http://blog.buildingautomationmonthly.com/what-is-tridium/, May 12, 2013.
Zito, "What is Tridium Part 2," http://blog.buildingautomationmonthly.com/tridium-part-2/, Sep. 10, 2013.
International Search Report and Written Opinion dated Jul. 17, 2018 for International PCT Application No. PCT/US2018/025189 (12 pages).
"Data analytics and smart buildings increase comfort and energy efficiency", https://www.microsoft.com/itshowcase/Article/Content/845/Data-analytics-and-smart-buildings-increase-comfort-and-energy-efficiency, Dec. 19, 2016, 8 pages.
Donnelly, "Building Energy Management: Using Data as a Tool", http://www.buildingefficiencyinitiative.org/sites/default/files/legacy/InstituteBE/media/Library/Resources/Existing-Building-Retrofits/Using-Building-Data-as-a-Tool.pdf, Oct. 2012, 9 pages.
"ASHRAE Dashboard Research Project," 29 pages, Aug. 28, 2008.
Honeywell, "Energy Manager User Guide," Release 3.2, 180 pages, 2008.
"Fuzzy Logic Toolbox 2.1, Design and Stimulate Fuzzy Logic Systems," The MathWorks, 2 pages, May 2004.
"Junk Charts, Recycling Chartjunk as junk art," 3 pages, Oct. 2, 2006.
"Model Predictive Control Toolbox 2, Develop Internal Model-Based Controllers for Constrained Multivariable Processes," The MathWorks, 4 pages, Mar. 2005.
Honeywell, "Product Guide 2004," XP-002472407, 127 pages, 2004.
"Statistics Toolbox, for Use with Matlab," User's Guide Version2, The MathWorks, 408 pages, Jan. 1999.
"Vykon Energy Suite Student Guide," Tridium Inc., 307 pages, Mar. 3, 2006.
"Web Based Energy Information Systems for Energy Management and Demand Response in Commercial Buildings," California Energy Commission, 80 pages, Oct. 2003.
Andover Controls, Network News, vol. 2, No. 2, 8 pages, 1997.
Andover Controls World, 4 pages, Spring 1997.
Bell et al., "Early Event Detection-Results from A Prototype Implementation," AICHE Spring National Meeting, 15 pages, Apr. 2005.
CADGRAPHICS, "The CADGRAPHICS User's Guide," 198 pages, 2003.
Carrier Comfort Network CCN Web, "Web Browser User Interface to the Carrier Comfort Network," 2 pages, 2002.
Carrier Comfort Network CCN Web, Overview and Configuration Manual, 134 pages, Apr. 2006.
Carrier Comfort Network CCN Web, Product Data, 2 pages, Apr. 2006.
Carrier, "i-Vu Powerful and Intuitive Front End for Building Control," 2 pages, Aug. 2005.
Carrier, "i-Vu Web-Based Integrated Control System," 3 pages, 2005.
Carrier, Demo Screen Shots, 15 pages, prior to Aug. 27, 2007.
Carrier, i-Vu CCN 4.0, Owner's Guide, 20 pages, Jul. 2007.
Carrier, i-Vu CCN, 7 pages, 2007.
Chan, "Rank Revealing QR Factorizations," Linear Algebra and It's Applications, vol. 88-89, p. 67-82, Apr. 1987.
Circon, "i-Browse Web-Based Monitoring and Control for Facility Management," 2 pages, prior to Aug. 27, 2007.
Australian Application 2009904740, Published copy, 28 pages, Application Filed on Sep. 29, 2009.
Echelon, "Energy Control Solutions with the i.Lon SmartServer," 4 pages, 2007.
Echelon, "i.Lon 100e3 Internet Server Models 72101R-300, 72101R-308, 72102R-300, 72103-R300 . . . " 5 pages, copyright 2002-2007.
Echelon, "i.Lon 100e3 Internet Server New Features," 15 pages, Sep. 2006.
Echelon, "i.Lon SmartServer," 5 pages, 2007.
Honeywell News Release, "Honeywell's New Sysnet Facilities Integration System for Boiler Plant and Combustion Safety Processes," 4 pages, Dec. 15, 1995.
Honeywell, "Excel Building Supervisor-Integrated R7044 and FS90 Ver. 2.0," Operator Manual, 70 pages, Apr. 1995.
Honeywell Home and Building Control Bulletin, "Introduction of the S7350A Honeywell WebPAD Information Appliance," 2 pages, Aug. 29, 2000; Picture of WebPad Device with touch screen, 1 Page; and screen shots of WebPad Device, 4 pages.
Honeywell, Excel 15B W7760B Building Manager Release 2.02.00, Installation Instructions, 28 pages, Dec. 2004.
Honeywell, The RapidZone Solution, Excel 5000 Open System, Application Guide, 52 pages, Jan. 2004.
"Remote Building Monitoring and Operations Home Page," 5 pages, prior to Aug. 27, 2007.
"Carrier: i-Vu CCN," 1 page, printed Mar. 11, 2008.
Carrier: 33CSCCNWEB-01 CCN Web Internet Connection to the Carrier Comfort Network, 1 page, printed Mar. 11, 2008.
"Products," 5 pages, printed Jul. 3, 2007. http://www.docs.hvacpartners.com/idc/groups/public/documents/techlit/gs-controls-ivuccn.rtf.
Lightstat Incorporated, "Internet Programmable Communicating Thermostats," 1 page, printed Mar. 13, 2007. http://www.lightstat.com/products/istat.asp.
Sharp, "Actius RD3D Desktop Replacement Notebook with Industry-Breakthrough 3D Screen," 1 page, printed Jun. 16, 2005. http://www.sharpsystems.com/products/pc_notebooks/actius/rd/3d/.
"Lights on a Wireless Lighting Control System," 11 pages, printed Mar. 22, 2007 http://www2.sims.berkeley.edu/courses/is213/s06/projects/lightson;final.html.

(56) References Cited

OTHER PUBLICATIONS

I.Lon 100e3 Internet Server, 1 page, prior to Aug. 27, 2007.
I.Lon, SmartServer, 2 pages, prior to Aug. 27, 2007.
I-stat, Demo Screen Shots, 9 pages, printed Mar. 13, 2007.
I-stat, The Internet Programmable Thermostat, 2 pages, prior to Aug. 27, 2007.
Ball, "Green Goal of 'Carbon Neutrality' Hits Limit," TheWall Street Journal, 7 pages, Dec. 30, 2008.
Network Integration Engine (NIE), Johnson Controls, 3 pages, Nov. 9, 2007.
Network Integration Engine (NIE), Product Bulletin, Johnson Controls, pp. 1-11, Jan. 30, 2008.
Kourti, "Process Analysis and Abnormal Situation Detection: From Theory to Practice," IEEE Control Systems Magazine, p. 10-25, Oct. 2002.
Mathew, "Action-Oriented Benchmarking, Using CEUS Date to Identify and Prioritize Efficiency Opportunities in California Commercial Buildings," 26 pages, Jun. 2007.
Morrison et al., "The Early Event Detection Toolkit," Honeywell Process Solutions, 14 pages, Jan. 2006.
Narang, "WEBARC: Control and Monitoring of Building Systems Over the Web," 53 pages, May 1999.

\* cited by examiner

METHODS AND SYSTEMS FOR REDUCING A RISK OF SPREAD OF DISEASE AMONG PEOPLE IN A SPACE

This application claims the benefit of U.S. Provisional Application No. 63/042,414, filed Jun. 22, 2020, which is hereby incorporated by reference.

TECHNICAL FIELD

The disclosure generally relates to health monitoring systems, and more particularly to systems and methods and systems for reducing a risk of spread of disease among occupants in a space.

BACKGROUND

Infectious diseases can spread through person to person contact as well as through the touching of contaminated surfaces. What would be desirable are systems and methods to help limit the spread of a disease within a space.

SUMMARY

The disclosure generally relates to health monitoring systems, and more particularly to systems and methods and systems for reducing a risk of spread of disease among occupants in a space. In one example, a method for counting a number of people in a space of a building may comprise storing a background image of a field of view of a video camera, receiving a video stream from the video camera, subtracting the background image from each frame of the video stream to identify one or more blobs in the field of view of the video camera, determining a distance between the video camera and each of the one or more blobs, and comparing a size of each of the one or more blobs to an expected size of a person at the determined distance of the corresponding blob. When the size of the blob is greater than the expected size of a person at the determined distance of the corresponding blob by more than a predetermined threshold, counting the blob as two or more people, otherwise counting the blob as one person or no person. The method may further comprise determining a count of the number people in the field of view of the video camera based at least in part on the count of people assigned to each of the one or more blobs.

In some cases, the predetermined threshold is when the blob may be greater by more than 1.5 times the expected size of a person at the determined distance of the corresponding blob.

In some cases, when the size of the blob is not greater than the expected size of a person at the determined distance of the corresponding blob by more than the predetermined threshold, deep learning may be used to determine whether to count the blob as one person or no person.

In some cases, the field of view of the video camera may cover only part of the space of the building and a field of view of one or more other video cameras cover one or more other parts of the space. The method may further comprise determining a count of the number people in the field of view of each of the one or more other video cameras and aggregating the counts of the number of people from all of the video cameras that have a field of view that covers part of the space to identify a total count of the number of people in the space.

In some cases, the method may further comprise updating the total count of the number of people in space at predetermined time intervals to obtain a plurality of total counts over a period of time.

In some cases, the method may further comprise determining a rate of change of the total count of the number of people in the space.

In some cases, the method may further comprise displaying a map of the one or more spaces of the building and shading each of the one or more spaces of the map based on the determined rate of change the total count of the number of people in the corresponding space.

In another example, a method for reducing a risk of spread of an illness in a building may comprise receiving a request from a user to use a common area of the building, counting a number of people in the common area. If the number of people in the common area is less than a threshold number, a virtual space may be allocated in the common area for the user. The method may further comprise providing a map including a route from a current location of the user to the common area that minimizes interactions with other users.

In some cases, allocating the virtual space may include indicating a predetermined length of occupancy time for the user to occupy the common area.

In some cases, if upon receipt of the request, the number of people in the common area is greater than the threshold number of a people, a notification may be provided for the user to wait a predetermined length of waiting time.

In some cases, the predetermined length of waiting time may be determined, at least in part, by a number of other users in queue to use the common area.

In some cases, the route may be updated in real time as the user moves to the common area to minimize interaction with other users.

In some cases, the method may further comprise transmitting an alert to one or more users in the common area indicating that one or more additional users are waiting to use the common area.

In some cases, a location of one or more users in the building may be determined using a location of a mobile device associated with each of the one or more users.

In some cases, a location of one or more users in the building is determined using a location tracker embedded in a piece of personal protective equipment associated with each of the one or more users.

In some cases, the method may further comprise displaying a location of one or more users in the building on the map.

In another example, a method for determining an arrangement of a group of people in a space may comprise capturing an image of the space, identifying a size of the space, and displaying a pattern in which a group of people can occupy the space while maintaining a predetermined distance between each person.

In some cases, the method may further comprise updating the pattern based on how many people are in the group of people.

In some cases, the method may further comprise transmitting an alert if there is no pattern that will allow the number of people in the group of people to occupy the space while maintaining the predetermined distance between each person.

In some cases, the pattern may include a representation of any furniture in the space and the people occupying the space.

The preceding summary is provided to facilitate an understanding of some of the features of the present disclosure and is not intended to be a full description. A full appreciation of the disclosure can be gained by taking the entire specification, claims, drawings, and abstract as a whole.

BRIEF DESCRIPTION OF THE DRAWINGS

The disclosure may be more completely understood in consideration of the following description of various embodiments in connection with the accompanying drawings, in which.

Figure 1:
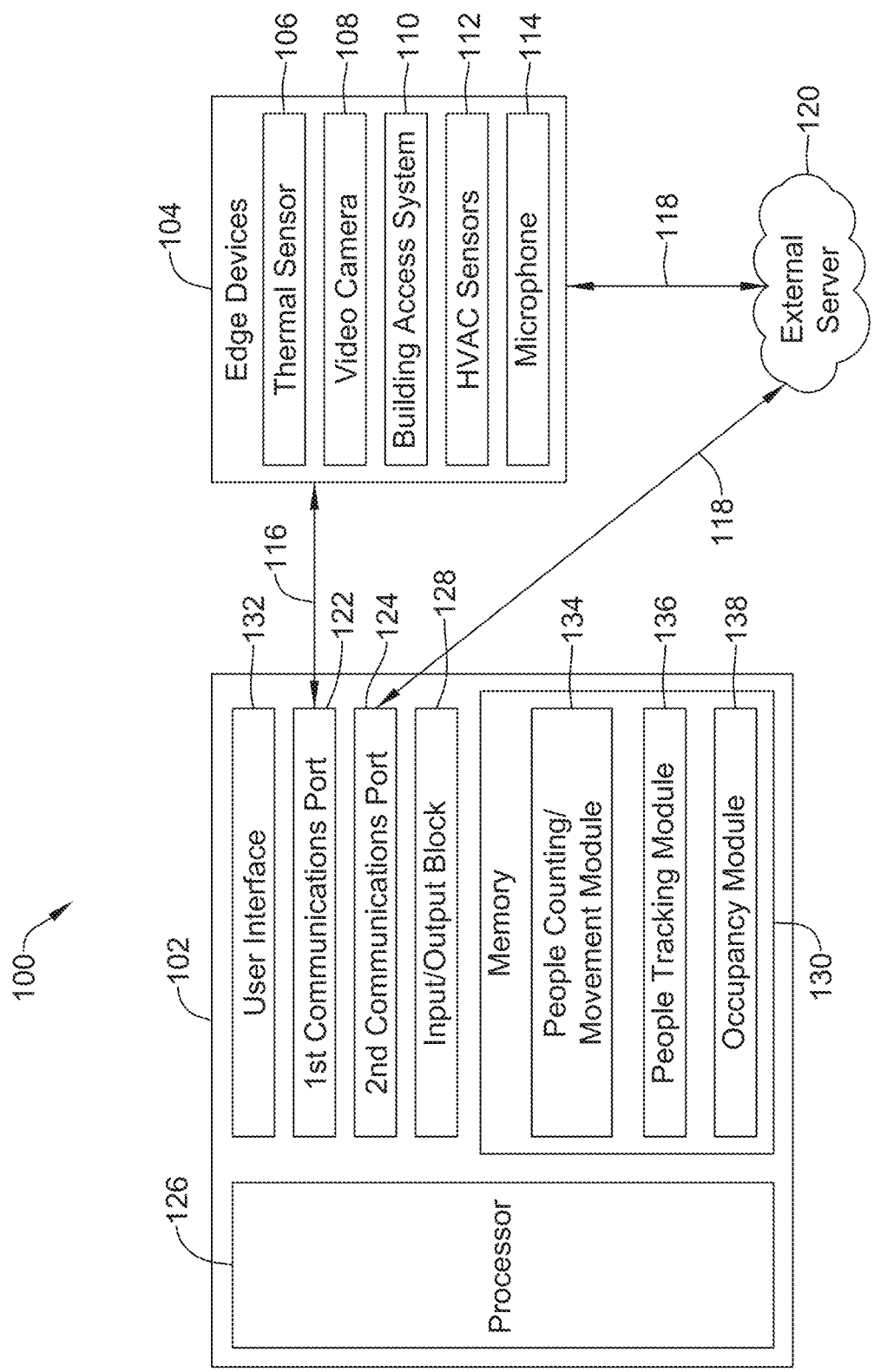
FIG. 1 is a schematic block diagram of an illustrative system for counting people, tracking people, and/or determining an occupancy of a space.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DESCRIPTION

The following detailed description should be read with reference to the drawings in which similar elements in different drawings are numbered the same. The description and the drawings, which are not necessarily to scale, depict illustrative embodiments and are not intended to limit the scope of the disclosure. The illustrative embodiments depicted are intended only as exemplary. Some or all of the features of any illustrative embodiment can be incorporated into other illustrative embodiments unless clearly stated to the contrary.

The various systems and/or methods described herein may be implemented or performed with a general purpose processor, a digital signal processor (DSP), an application specific integrated circuit (ASIC), a field programmable gate array signal (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

In some cases, methods or systems may utilize a dedicated processor or controller. In other cases, methods or systems may utilize a common or shared controller. Whether a system or method is described with respect to a dedicated controller/processor or a common controller/processor, each method or system can utilize either or both a dedicated controller/processor or a common controller/processor. For example, a single controller/processor can be used for a single method or system or any combination of methods or systems. In some cases, system or method may be implemented in a distributed system, where parts of the system or method are distributed among various components of the distributed system. For example, some parts of a method may be performed locally, while other parts may be performed by a remote device such as a remote server. These are just examples.

Infectious diseases may be transmitted from person to person or by coming into contact with surfaces that have been contaminated with the contagion, among other transmission modalities. During times of increased prevalence of illness, such as cold and flu season, during an epidemic or pandemic, or other times, it may be desirable to track the location and nearness of people within a building or space and/or to limit a number of people in a space. The systems and methods described herein may be applicable to a wide variety of environments, including, but not limited to, hospitals, senior care facilities, nursing homes, restaurants, hotels, office buildings, arenas, public transit depots, public transit vehicles, outdoor parks, etc.

In some cases, buildings or public areas may include existing building management systems, such as Heating, Ventilation and/or Air Conditioning (HVAC) and/or surveillance systems. It is contemplated that the data acquired from these and other systems may be used alone or in combination with other data acquisition devices to, for example, monitor the position of people, nearness of a person to other people, a number of people in a space, and/or any other suitable parameter.

FIG. 1 is a schematic block diagram of an illustrative system 100 for counting a number of people in a space. The system 100 may form a part of or be used in combination with a building management system (BMS). Some illustrative systems that may form a part of a BMS include, but are not limited to, heating, ventilation, and air conditioning (HVAC) systems, security and/or surveillance systems, lighting systems, fire suppression systems, access control systems, etc. An illustrative BMS is described in commonly assigned U.S. Provisional Patent Application, titled OCCUPANT HEALTH MONITORING FOR BUILDINGS, the disclosure of which is hereby incorporated by reference. In other examples, the system 100 may be a stand-alone system. It is further contemplated that the system 100 may be used in areas outside of a traditional building, such as, but not limited to, public transit, parks, and/or other areas where people may gather. In some cases, the system 100 can control one or more of an HVAC system, a security system, a lighting system, a fire system, a building access system and/or any other suitable building control system as desired, but this is not required.

In some cases, the system 100 includes a controller 102 and one or more edge devices 104. The edge devices 104 may include, but are not limited to, thermal sensors 106, still or video cameras 108, building access system readers or devices 110, HVAC sensors 112, microphones 114, and/or other BMS devices or sensors. Some illustrative HVAC sensors 112 may include, but are not limited to, temperatures sensors, humidity sensors, carbon dioxide sensors, pressure sensors, occupancy sensors, proximity sensors, etc. The controller 102 may be configured to receive data from the edge devices 104, analyze the data, and make decisions based on the data, as will be described in more detail herein. For example, the controller 102 may include control circuitry and logic configured to operate, control, command, etc. the various components (not explicitly shown) of the control system 100 and/or issue alerts or notifications.

The controller 102 may be in communication with any number of edge devices 104 as desired, such as, but not limited to, one, two, three, four, or more. In some cases, there may be more than one controller 102, each in communication with a number of edge devices. It is contemplated that the number of edge devices 104 may be dependent on the size and/or function of the system 100. The edge devices 104 may be selected and configured to monitor differing aspects of the building and/or area of the system 100. For example, some of the edge devices 104 may be located interior of the building. In some cases, some of the edge devices 104 may be located exterior to the building. Some of the edge devices 104 may be positioned in an open area, such as a park or public transit stop. These are just some examples.

The controller 102 may be configured to communicate with the edge devices 104 over a first network 116, including a local area network (LAN) or a wide area network (WAN), or the connection may be made to an external computer (for example, through the Internet using an Internet Service Provider). Such communication can occur via a first communications port 122 at the controller 102 and a communication interface (not explicitly shown) at the edge devices 104. The first communications port 122 of the controller 102 and/or the communication interfaces of the edge devices 104 can be a wireless communications port including a wireless transceiver for wirelessly sending and/or receiving signals over a wireless network 116. However, this is not required. In some cases, the first network 116 may be a wired network or combinations of a wired and a wireless network.

The controller 102 may include a second communications port 124 which may be a wireless communications port including a wireless transceiver for sending and/or receiving signals over a second wireless network 118. However, this is not required. In some cases, the second network 118 may be a wired network or combinations of a wired and a wireless network. In some embodiments, the second communications port 124 may be in communication with a wired or wireless router or gateway for connecting to the second network 118, but this is not required. When so provided, the router or gateway may be integral to (e.g., within) the controller 102 or may be provided as a separate device. The second network 118 may be a wide area network or global network (WAN) including, for example, the Internet, wireless 4/5G, LTE, and/or any other suitable network. The controller 102 may communicate over the second network 118 with an external web service hosted by one or more external web servers 120 (e.g. the cloud).

The controller 102 may include a processor 126 (e.g., microprocessor, microcontroller, etc.) and a memory 130. In some cases, the controller 102 may include a user interface 132 including a display and a means for receiving user input (e.g., touch screens, buttons, keyboards, etc.). The memory 130 may be in communication with the processor 126. The memory 130 may be used to store any desired information such as, but not limited to, control algorithms, configuration protocols, set points, schedule times, diagnostic limits such as, for example, differential pressure limits, delta T limits, security system arming modes, and the like. In some embodiments, the memory 130 may include specific control programs or modules configured to analyze data obtained from the edge devices 104 for a particular condition or situation. For example, the memory 130 may include, but is not limited to, a people counting and/or movement module 134, a people tracking module 136, and/or an occupancy module 138. Each of these modules 134, 136, 138 may be configured to help minimize contact between individuals that may contribute to the spread of a disease. The memory 130 may include one or more of the modules 134, 136, 138. In some cases, the memory 130 may include additional modules beyond those specifically listed. The memory 130 may be any suitable type of storage device including, but not limited to, RAM, ROM, EPROM, flash memory, a hard drive, and/or the like. In some cases, the processor 126 may store information within the memory 130, and may subsequently retrieve the stored information from the memory 130.

In some embodiments, the controller 102 may include an input/output block (I/O block) 128 having a number of wire terminals for receiving one or more signals from the edge devices 104 and/or system components and/or for providing one or more control signals to the edge devices 104 and/or system components. For example, the I/O block 128 may communicate with one or more components of the system 100, including, but not limited to, the edge devices 104. The controller 102 may have any number of wire terminals for accepting a connection from one or more components of the system 100. However, how many wire terminals are utilized and which terminals are wired is dependent upon the particular configuration of the system 100. Different systems 100 having different components and/or types of components may have different wiring configurations. In some cases, the I/O block 128 may be configured to receive wireless signals from the edge devices 104 and/or one or more components or sensors (not explicitly shown). Alternatively, or in addition to, the I/O block 128 may communicate with another controller. It is further contemplated that the I/O block 128 may communicate with another controller which controls a separate building control system, such as, but not limited to a security system base module, an HVAC controller, etc.

In some cases, a power-transformation block (not explicitly shown) may be connected to one or more wires of the I/O block 128, and may be configured to bleed or steal energy from the one or more wires of the I/O block 128. The power bled off of the one or more wires of the I/O block may be stored in an energy storage device (not explicitly shown) that may be used to at least partially power the controller 102. In some cases, the energy storage device may be capacitor or a rechargeable battery. In addition, the controller 102 may also include a back-up source of energy such as, for example, a battery that may be used to supplement power supplied to the controller 102 when the amount of available power stored by the energy storage device is less than optimal or is insufficient to power certain applications.

Certain applications or functions performed by the base module may require a greater amount of energy than others. If there is an insufficient amount of energy stored in the energy storage device then, in some cases, certain applications and/or functions may be prohibited by the processor 126.

The controller 102 may also include one or more sensors such as, but not limited to, a temperature sensor, a humidity sensor, an occupancy sensor, a proximity sensor, and/or the like. In some cases, the controller 102 may include an internal temperature sensor, but this is not required.

The user interface 132, when provided, may be any suitable user interface 132 that permits the controller 102 to display and/or solicit information, as well as accept one or more user interactions with the controller 102. For example, the user interface 132 may permit a user to locally enter data such as control set points, starting times, ending times, schedule times, diagnostic limits, responses to alerts, associate sensors to alarming modes, and the like. In one example, the user interface 132 may be a physical user interface that is accessible at the controller 102, and may include a display and/or a distinct keypad. The display may be any suitable display. In some instances, a display may include or may be a liquid crystal display (LCD), and in some cases an e-ink display, fixed segment display, or a dot matrix LCD display. In other cases, the user interface may be a touch screen LCD panel that functions as both display and keypad. The touch screen LCD panel may be adapted to solicit values for a number of operating parameters and/or to receive such values, but this is not required. In still other cases, the user interface 132 may be a dynamic graphical user interface.

In some instances, the user interface 132 need not be physically accessible to a user at the controller 102. Instead, the user interface may be a virtual user interface 132 that is accessible via the first network 116 and/or second network 118 using a mobile wireless device such as a smart phone, tablet, e-reader, laptop computer, personal computer, key fob, or the like. In some cases, the virtual user interface 132 may be provided by an app or apps executed by a user's remote device for the purposes of remotely interacting with the controller 102. Through the virtual user interface 132 provided by the app on the user's remote device, the user may change control set points, starting times, ending times, schedule times, diagnostic limits, respond to alerts, update their user profile, view energy usage data, arm or disarm the security system, configured the alarm system, and/or the like.

In some instances, changes made to the controller 102 via a user interface 132 provided by an app on the user's remote device may be first transmitted to an external web server 120. The external web server 120 may receive and accept the user inputs entered via the virtual user interface 132 provided by the app on the user's remote device, and associate the user inputs with a user's account on the external web service. If the user inputs include any changes to the existing control algorithm including any temperature set point changes, humidity set point changes, schedule changes, start and end time changes, window frost protection setting changes, operating mode changes, and/or changes to a user's profile, the external web server 120 may update the control algorithm, as applicable, and transmit at least a portion of the updated control algorithm over the second network 118 to the controller 102 where it is received via the second port 124 and may be stored in the memory 130 for execution by the processor 126. In some cases, the user may observe the effect of their inputs at the controller 102.

Rather than a dedicated app, the virtual user interface 132 may include one or more web pages that are transmitted over the second network 118 (e.g. WAN, the Internet, wireless 4/5G, LTE, etc.) by an external web server (e.g., web server 120). The one or more web pages forming the virtual user interface 132 may be hosted by an external web service and associated with a user account having one or more user profiles. The external web server 120 may receive and accept user inputs entered via the virtual user interface 132 and associate the user inputs with a user's account on the external web service. If the user inputs include changes to the existing control algorithm including any control set point changes, schedule changes, start and end time changes, window frost protection setting changes, operating mode changes, and/or changes to a user's profile, the external web server 120 may update the control algorithm, as applicable, and transmit at least a portion of the updated control algorithm over the second network 118 to the controller 102 where it is received via the second port 124 and may be stored in the memory 130 for execution by the processor 126. In some cases, the user may observe the effect of their inputs at the controller 102.

In some cases, a user may use either a user interface 132 provided at the controller 102 and/or a virtual user interface as described herein. These two types of user interfaces are not mutually exclusive of one another. In some cases, a virtual user interface 132 may provide more advanced capabilities to the user. It is further contemplated that a same virtual user interface 132 may be used for multiple BMS components.

During times of a pandemic or other times when illnesses are easily spread, it may be desirable to know a number of people in a building or space, the spaces or zones that are more densely populated and/or how the people are moving throughout the building or spaces. In some cases, it may be desirable to count a number of people in the building or space by analyzing a video stream. While some overhead cameras may be used to count people in certain spaces, overhead cameras may not be as available throughout a space as non-overhead cameras. To limit capital costs, it may be desirable to utilize non-overhead cameras where overhead cameras are not available. However, in some cases, overlap of people in the field of view of a non-overhead cameras may result in too few people being counted, such as when one person is standing behind another person in the field of view of the camera.

Figure 2:
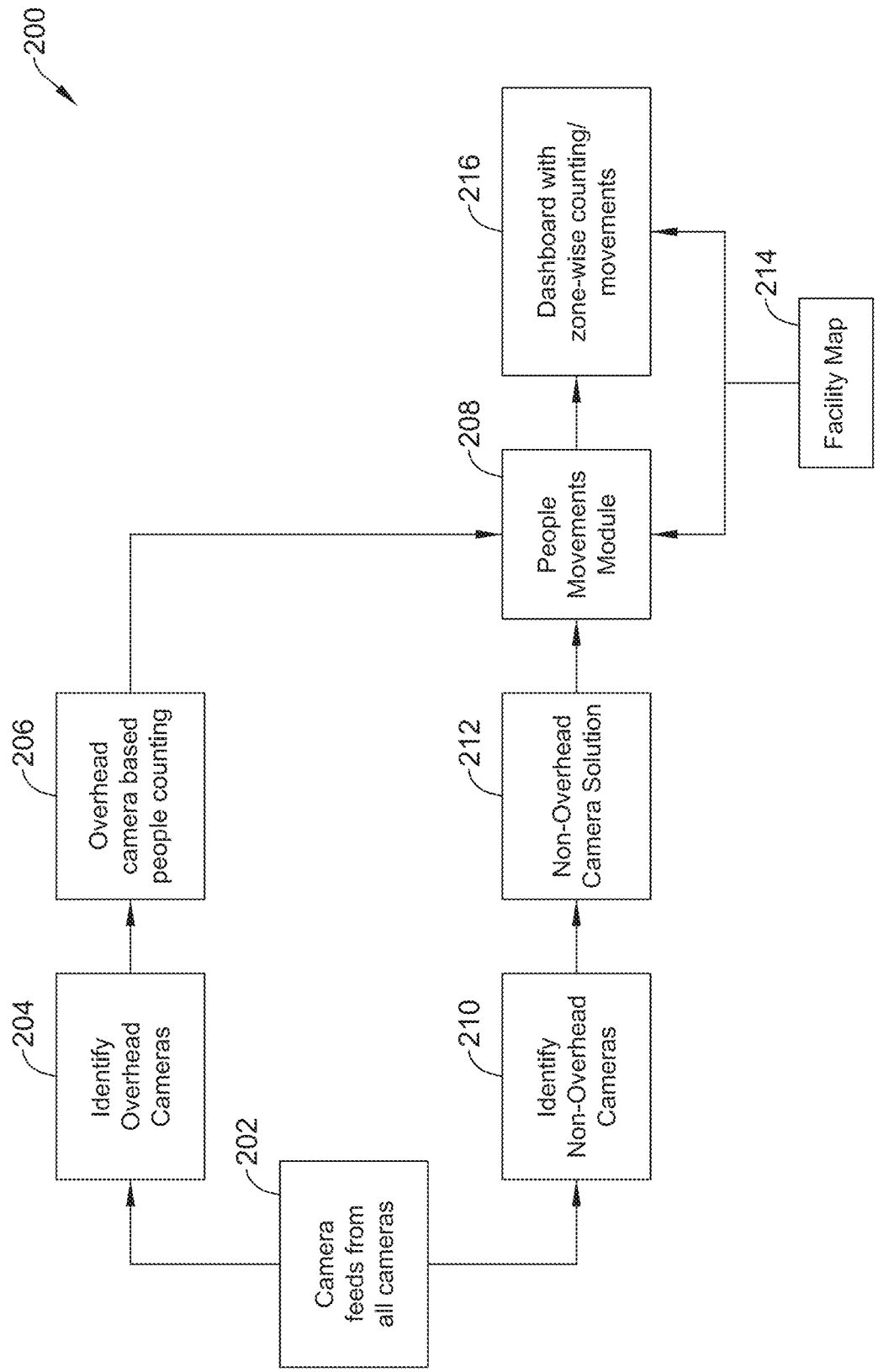
FIG. 2 is a block diagram of an illustrative system for using overhead and/or non-overhead cameras to count people in a space.

FIG. 2 is an illustrative block diagram of a system 200 for using overhead and/or non-overhead cameras to count people in a space of a building. The building or space may be a commercial office building, a factory, a hotel, a hospital, restaurants, shopping centers, moving vehicles (e.g., buses, trains, planes, etc.) and/or any other space. The system 200 may be a stand-alone system or may be incorporated into or used with other systems such as a building management system. Generally, the system 200 may include a video analytics module or people movement module 214 that is configured to detect or determine a number of people in a space and/or a rate of change of a number of people in the space. The people movement module 214 may be the same as or similar to the people counting and/or movement module 134 described above.

The system 200 may include a controller, which may be a part of the controller 102 described above, that is in communication with a plurality of edge devices 104, such as, but not limited to, video cameras 108 and/or access control devices 110. In other cases, the controller may be a separate controller form the controller 102 described above.

The edge devices 104 may be located within the building or space and/or external to the building (e.g., at an entrance to the building). Generally, the controller 102 may receive one or more video feeds 202 from one or more cameras. In some cases, the video feed 202 may be a visible light video, a thermal image video, or combination thereof. The video feed 202 may be acquired from an overhead camera or a non-overhead camera, as desired. As used herein, an overhead camera is one that is positioned on a ceiling or other location where the field of view is such that people standing in close proximity are readily differentiated from one another. A non-overhead camera may be positioned on a wall or other location where the field of view is such that a person who is standing behind another person (relative to the camera) may be obscured or partially obscured in the resulting video stream. The video feed 202 may be acquired from one or more overhead and/or non-overhead cameras, as desired. While the system 200 is shown and described as including both overhead and non-overhead cameras, it is contemplated that in some cases only one type of video camera 108 may be present.

The controller 102 may first identify which of the video feeds 202 are from overhead cameras 204 and which are from non-overhead cameras 210. For example, the controller 102 may utilize different people counting algorithms based on the type of camera. Video feeds 202 which originated from overhead cameras 204 may be analyzed using a people counting algorithm 206 specific to overhead cameras 204 to determine a number of people in a particular space. The number of people in a particular space is then provided to the people movement module 208.

Figure 3:
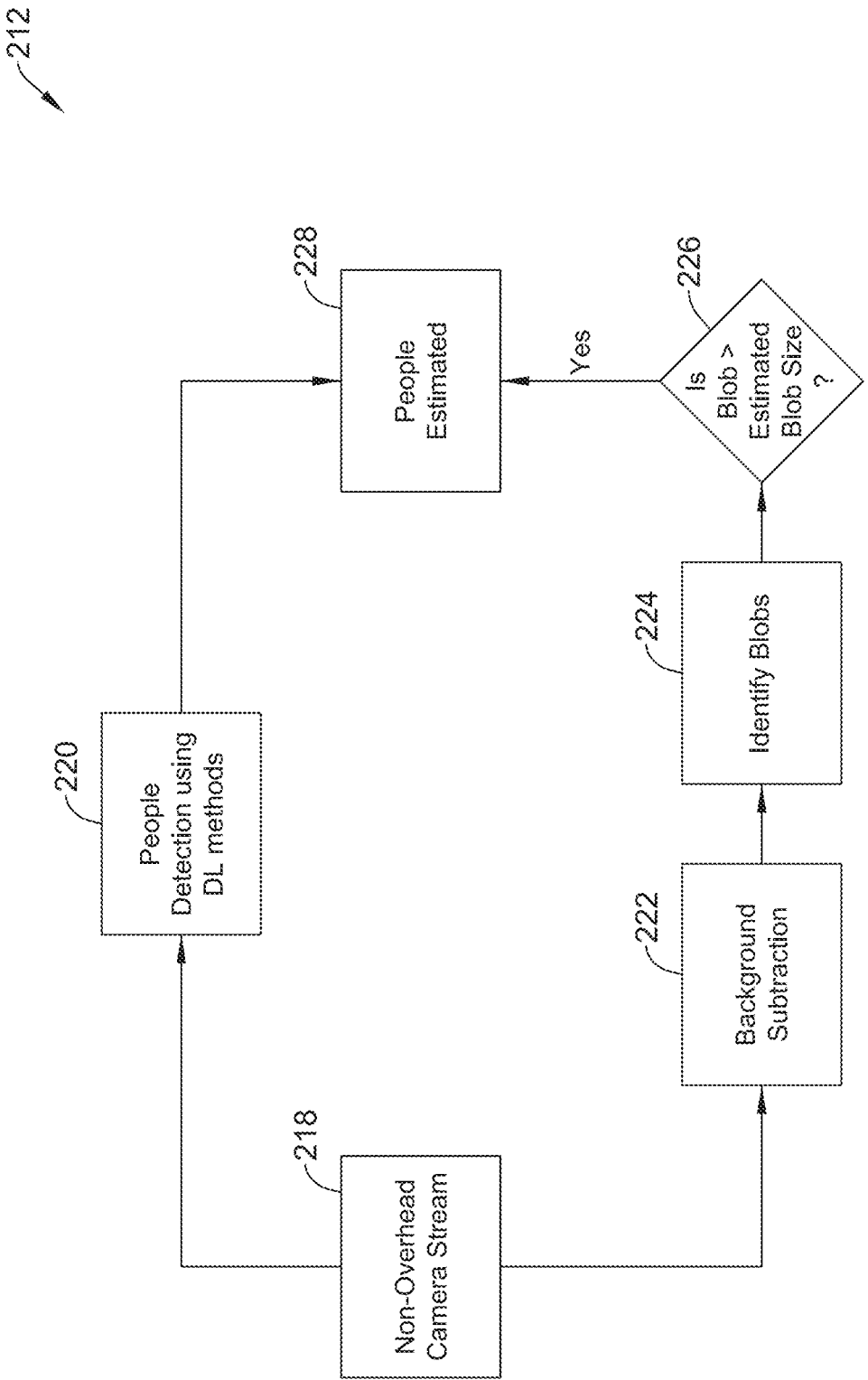
FIG. 3 is a flow chart of an illustrative people counting algorithm applied to non-overhead cameras.

Video feeds 202 which originated from non-overhead cameras 210 may be analyzed using a people counting algorithm 212 specific to non-overhead cameras 210 to determine a number of people in a particular space. FIG. 3 is a flow chart of an illustrative people counting algorithm 212 applied to non-overhead cameras 210. The video streams 218 originating from non-overhead cameras 210 may be analyzed in two different ways. For example, the controller 102 may utilize artificial intelligence such as deep learning methods 220 to determine a number of people that are present in the field of view and are added to the people count 228. In some cases, deep learning may be used to analyze the overall shape of objects detected to look for heads, limbs, shoulders, etc. These shapes may then be used to determine if one or more persons are present in the space. If people are occluded (e.g., behind another person) beyond for example 30-50%, deep learning based methods may not produce accurate results. For example, in some cases, two people may be counted as a single person. The illustrative people counting algorithm 212 combines deep learning based analysis 220 and computer vision methods to get the most probable number of people in the space.

In concert with performing the deep learning based analysis 220, the controller 102 may perform a background subtraction 222 on each frame of the video stream 218. In some cases, a background image of the field of view of the video camera 210 is stored in the memory 130 of the controller 102 to facilitate the background subtraction 222. Once the background has been subtracted, any remaining objected may be identified as a potential person and may be seen as one or more blobs 224. The controller 102 may be configured to determine a distance between the camera 210 and each of the one or more blob 224. In some cases, the system 200 may undergo a calibration phase so that the distance between blobs 224 and the camera 210 within the field of view of the camera 210 can be accurately determined. For example, during the calibration phase, the controller 102 may be trained with a person standing at a plurality of known distances from the camera 210. This may allow the controller 102 to determine an expected blob size of a single person at the particular distance. In some cases, the calibration procedure may be repeated a number of different times using different persons of different shapes and sizes to generate a plurality of estimated blob sizes. The plurality of estimated blob sizes may be averaged to determine an average expected blob size for a plurality of different distances.

Figure 4:
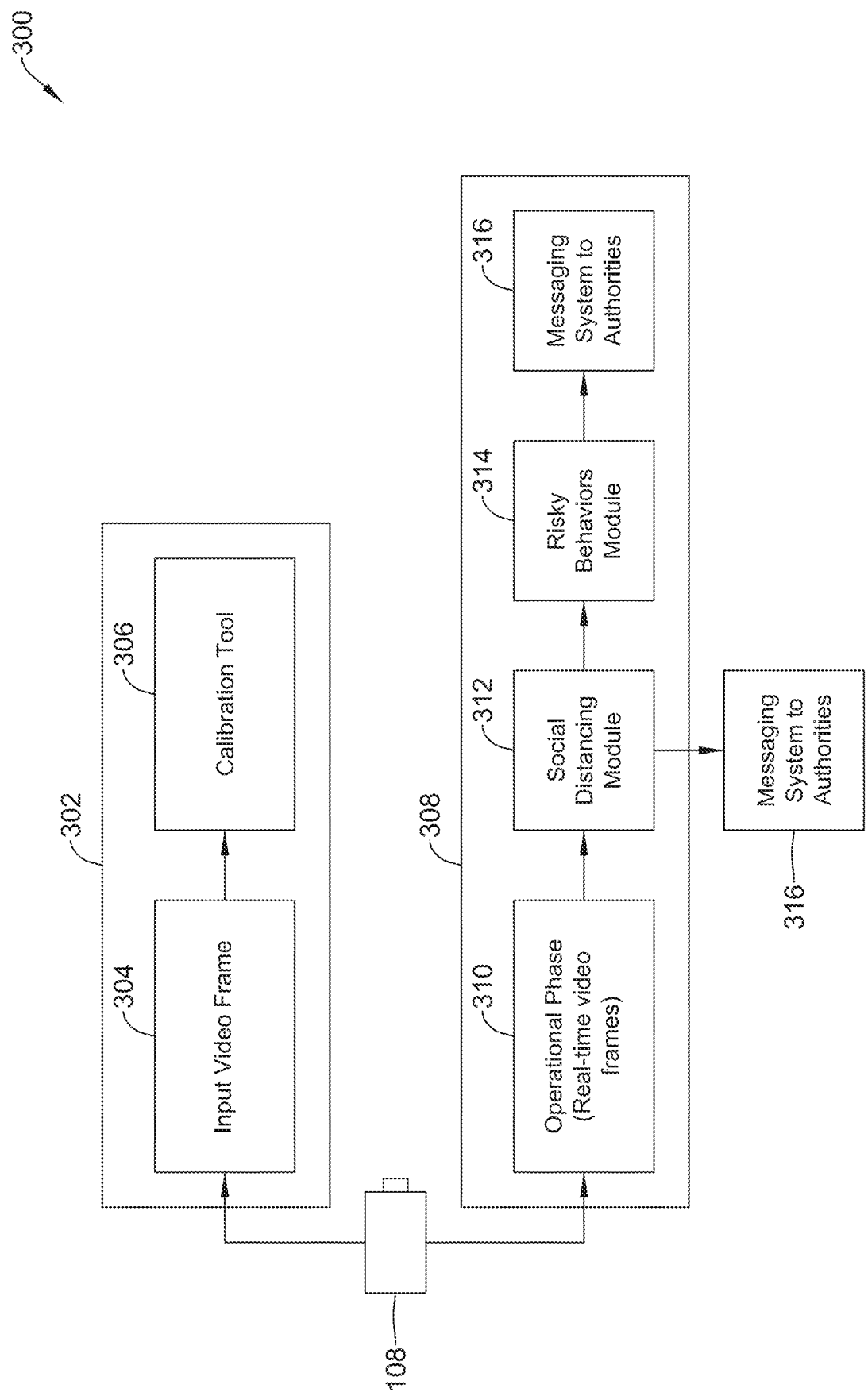
FIG. 4 is a block diagram of an illustrative system for detecting if occupants of a building or space are following social distancing guidelines or if they are engaging in behaviors that may be deemed risky in a particular environment.

In some cases, to calibrate the camera, a frame of the video may be input into a calibration tool (see FIG. 4). The calibration tool may use any of a number of different calibration techniques in order to determine distances within the field of view. In one example, the calibration tool may determine the area or number of pixels of a known-sized object at a near end and a far end of the camera view. Using this information, the calibration tool can generate a 3D map of the perspective view including distances and sizes. In some cases, a user may enter the dimensions of the known sized object, although this is not required. In another example, the calibration tool or a user may select at least four points (e.g., forming a rectangle) on the ground plane visible in the image. The length and width of the rectangle may be provided (e.g., via user input). This information may then be used to map the perspective view to a bird's eye view. The length and width values of the rectangle to correspond to the x- and y-axis pixel resolution of these values. Once the calibration is complete, the calibration values may be stored in the memory.

Regardless of how the camera is calibrated, the blob 224 from the video frame may be compared to the expected blob size at the determined distance, as shown at block 226. Generally, when the size of the blob 224 is greater than the expected size of a person (e.g., the expected blob size as determined during calibration) at the determined distance of the blob 224, the blob 224 may be counted as two or more people, if the size of the blob is about equal to or less than the expected size of a person (e.g., the expected blob size as determined during calibration), the blob 224 may be counted as one person or no person. In some cases, the blob 224 may need to be a predetermined threshold greater than the expected blob size for the blob 224 to be counted as more than one person. In one example, if the blob 224 is 1.5 times or more than the expected blob size, the blob 224 is counted as two (or more) people. If the blob is less than 1.5 times or less than the expected blob size, the blob 224 is counted as one person, or in some cases, no persons.

If the blob 224 is greater than the expected blob size, the controller 102 may be configured to determine how many people are represented by the blob 224. As noted above, the background subtraction 222 and the remaining blob(s) 224 are used in concert with deep learning techniques 220. For example, the deep learning (DL) based analysis 220 may provide a number of people in the field of view of the camera 210 which can be preliminary estimated to give a first count ($NP_{DL}$). However, as noted above, this may not account for people that may be partially obscured in the field of view by other people. Thus, the controller 102 can perform the blob analysis to determine if the number of people in the field of view (PeopleEstimated) 228 should be changed. For example, if the blob 224 is determined to represent two people, the number of people estimated to be in the field of view should be increased by one. This accounts for the controller 102 having already counted one of the two people in the blob 224 using the deep learning based analysis 220.

For example, the number of people to be present in the field of view using both deep learning based analytics 220 and background subtraction 222 may be calculated as defined in Equation 1:

$$PeopleEstimated = \text{ceil}\left(\frac{EstimatedSize - ActualSize}{EstimatedSize}\right) + NP_{DL} \quad \text{Equation 1}$$

where the EstimatedSize is the expected size of a person at the same distance from the camera (as the current blob) as determined during calibration, the ActualSize is the size of the current blob 224, ceil is a command to round up or down to the nearest whole number, and $NP_{DL}$ is the number of people detected utilizing the deep learning based analysis 220. Thus, if the size of the blob 224 is greater than about 1.5 or more times than the expected size of the blob, the controller 102 may determine that there may be one or more extra person in the blob 224 that was not included in the deep learning based analysis 220. Thus, the people estimated to be in the field of view may be 1 plus the number of people determined in the deep learning based analysis 220 and this is taken into account when determining the estimated number of people 228 in the field of view of the camera 210. In some cases, people tracking may be utilized to facilitate people counting. For example, if a person leaves one room they would be expected to enter an adjacent room. If the people count did not increase by one in the adjacent room, this knowledge may be used to determine that a blob identified in the adjacent room likely represent three people, rather than just two.

In some cases, a field of view of a single non-overhead camera 210 may not be sufficient to determine a number of people in the space of a building with great accuracy. Thus, a count of people in the field of view of one or more additional cameras may be determined using the people counting algorithm 212. The people counts 228 from all of the video cameras 210 assigned to the space of the building (or that that view at least part of the space) may be aggregated to determine a total count of the number of people in the space. It is contemplated that the video cameras 210 may be assigned to a space or zone using a camera ID or other parameter.

Returning to FIG. 2, the people count 206 from the overhead camera(s) 204 (if so provided) and/or the people count 228 from the non-overhead camera(s) 228 may be provided to a people movement module 208. The people count 206, 228 may be updated and provided to the people movement module 208 at predetermined time intervals to obtain a plurality of total counts 206, 228 in a space over a period of time. The people movement module 208 may analyze the plurality of total counts 206, 228 over a period of time to determine a rate of change of the number of people in the space. The people movement module 208 may be configured to use all of the cameras 204, 210 for a specific space and the people counts 206, 228 determined from each camera 204, 210 when determining a number of people in the specific space and when determining the rate of change for the specific space. The controller 102 may be configured to display the rate of change of the number of people in each of a number of different spaces on a dashboard 216. The dashboard may be a display on a personal computer, a mobile computing device (e.g., a tablet or smartphone), a laptop, a security monitoring station, etc.

In some cases, the rate of change may be displayed in a tabular format. In other cases, the rate of change may be displayed on a facility map 214. For example, a facility map 214 may be stored in the memory 130 of the controller 102. The controller 102 may be configured to assign a color or shading to a particular space based on the rate of change of the number of people in the particular space. It is contemplated that the controller 102 may be provided with predetermined thresholds or ranges of rate changes for which each color is assigned. For example, a space with a low rate of change may be assigned a green color, a space with a moderate rate of change may be assigned an orange color, and a space with a high rate of change may be assigned a red color. Other colors and threshold levels may be used as desired. It is contemplated that the colors and/or shading of the facility map may be continually updated as the rates of the change vary throughout a day. For example, around a meal time, the rate of change of the total count of people in a breakroom may be high and thus the space may be displayed as red on a facility map while near the end of the working day, the rate change of the total count of people in the breakroom may be low and thus the space may be displayed as green. Identifying spaces or zone where a large number of people are entering and/or exiting may be useful in identifying those spaces or zones that are higher risk for the spread of a disease. Warning or alerts may be sent out warning occupants of the building of the higher risk spaces or zones and requesting that they wear Personal Protective Equipment (PPE) and/or to take extra care in practicing healthy behaviors such as social distancing and hand washing in these higher risk zones.

The facility map with the rate of change of the total count of people readily displayed may allow a user to quickly determine where the more risky zones in the building for spread of disease are located, thus allowing a user to take appropriate actions to limit people movement in these higher risk zones. In some cases, people movement may be limited by denying access requests to the zones by access control devices for a period of time. In some cases, the controller 102 may be configured to issue an alert when a predetermined threshold rate of change occurs. The alert may indicate a Standard Operating Procedure (SOP) that outlines steps that should be taken to reduce the flow of people in the higher risk zones, although this is not required.

In addition to showing live data, the controller 102 may be configured to display historical data on a timeline with the live data or separately in response to a user input. It is further contemplated that the controller 102 may be configured to perform predictive analytics on the historical rate of change data for a particular space to estimate movements based on previously acquired data. The predictive analytics may be displayed on the dashboard with the live data and/or historical data or separately in response to a user input. In some cases, the controller 102 may be configured to alert a user that a space is expected to experience higher rates of change before the rate of change actually occurs, although this is not required. It is contemplated that this may allow a user to proactively limit the number of people entering and/or exiting a space to reduce transmission of a disease.

In addition to knowing generally where people are in the building, it may be desirable to know if people (even if they are in small groups) are engaging in behavior that may contribute to the spread of an illness. FIG. 4 is a block diagram of an illustrative system 300 for detecting if occupants of a building or space are following social distancing guidelines or if they are engaging in behaviors that may be deemed risky in a particular environment. The building or space may be a commercial office building, a factory, a hotel, a hospital, restaurants, shopping centers, moving vehicles (e.g., buses, trains, planes, etc.) and/or any other space. The system 300 may be a stand-alone system or may be incorporated into or used with other systems such as a building control system. Generally, the system 300 analyze the distance between people along with the behavior of the people to determine if the people are standing too close or engaging in other risky behavior, such as, but not limited to, failure to wear appropriate PPE. The system 300 may include at least one video camera 108 for capturing images in a field of view. The video camera 108 may be a visible light camera, a thermal imaging camera, or a combination thereof.

Prior to operating the system 300, the system 300 may undergo a calibration phase 302. This may be performed so that the distance between people or objects within the field of view of the camera 108 can be accurately determined. To calibrate the camera, a frame of the video 304 may be input into a calibration tool 306. The calibration tool 306 may be stored in the memory 130 of the controller 102. The controller 102 may be the same controller as used for the people counting system 200 discussed above. In other cases, a separate controller may be provided. Alternatively, the calibration tool 306 may be stored and executed by an external server 120. The calibration tool 306 may use any of a number of different calibration techniques in order to determine distances within the field of view. In one example, the calibration tool 306 may determine the area or number of pixels of a known-sized object at a near end and a far end of the camera view. Using this information, the calibration tool 306 can generate a 3D map of the perspective view including distances and sizes. In some cases, a user may enter the dimensions of the known sized object, although this is not required. In another example, the calibration tool 306 or a user may select at least four points (e.g., forming a rectangle) on the ground plane visible in the image. The length and width of the rectangle may be provided (e.g., via user input). This information may then be used to map the perspective view to the bird's eye view. The length and width values of the rectangle to correspond to the x- and y-axis pixel resolution of these values. Once the calibration is complete, the calibration values may be stored in the memory. If the calibration has been performed by a remote server 120, the remote server may transmit the calibration values to the memory 130 of the controller 102. Alternatively, the controller 102 may download the calibration values from the remote server 120.

Once the calibration is complete, the camera 108 may be placed into an operational mode 308. In the operational mode, real time video is captured of a surveilled area and is transmitted to the controller 102. The controller 102 may then perform behavior analytics on the individuals identified in the captured video. Generally, the behavior analytics may include determining a risky behavior metric that identifies a measure of risky behavior of the individuals identified in the captured video that is based at least in part on a distance between two or more of the individuals identified in the captured video is below a predetermined distance threshold and/or a time that the distance between the two or more of the individuals is below a predetermined distance threshold exceeds a time threshold.

The video 310 may be analyzed by a social distancing module 312 that may be stored in a memory 130 of the controller 102. The social distancing module 312 may be configured to use person detection, face detection, background subtraction, etc. to first identify or isolate an individual or person in the captured video. When two or more people are within the field of view, the social distancing module 312 is configured to compute the distance between each of the detected people within the frame. The social distancing module 312 may then compare the computed distances to one or more predetermined acceptable distance thresholds. The distance thresholds may be user defined and user modifiable parameters. For example, in times of a pandemic, a distance threshold may be larger than in times of no pandemic. It is further contemplated that the distance threshold may vary based on the type of space being monitored. For example, a well ventilated indoor space may allow people to stand closer together than a poorly ventilated space. This is just one example. In some cases, the social distancing module 312 may use two or more tiered distance thresholds to determine how risky the behavior of the individuals is. For example, the closer the people are, the riskier the behavior and thus the higher the risky behavior metric. Also, the longer dwell time that people remain close together may increase the risky behavior metric.

The social distancing module 312 may calculate the number of people in the frame, the number of people adhering to the social distancing guidelines (e.g., spaced at least the threshold distance from one another), the number of people who are not in compliance with the social distancing guidelines (e.g., spaced at less than the threshold distance from one another for at least a minimum dwell time), the number of people who are not in compliance with PPE guidelines (if any), etc. to generate a risky behavior metric. In some cases, the risky behavior metric may be a weighted score, an analog score (e.g. on a scale of 0-100), a binary indicator (e.g., pass/fail, compliant/non-compliant), etc. In some cases, the risky behavior metric may increase the longer or more often the risky behavior occurs. It is contemplated that the behavior of any number of individuals within the video 310 may be analyzed. For example, if three or more individuals are identified in the video 310, the social distancing module may be configured to determine a distance between each of the three or more individuals in the video 310.

When the risky behavior metric exceeds a risk threshold, a real-time alert 316 may be generated. In the case of social distancing, the risk threshold may be that two or more people remained below the distance threshold for at least a predetermined length of time. However, other risk thresholds may be defined to suit a particular situation. In some cases, the alert 316 may be an audio alert transmitted directly to the monitored space and hence the people exhibiting non-compliance or the risky behavior. For example, the alert may instruct the two or more individuals to move apart. In other cases, a real-time audio or written alert (e.g., SMS or e-mail) may be transmitted to a remote device. The remote device may be a part of the building management system, a mobile device of a supervisor, etc. In some cases, the alert 316 may be displayed at the video surveillance monitoring station. The alert may include a location of the non-compliance and/or a number of people who are non-compliant. In some cases, the alert may include a recommended action, such as, but not limited to screening the non-compliant people for symptoms of an illness or providing a reminder of the health guidelines. In yet other embodiments, the alert 316 may identify the surveilled area where the risky behavior occurred as a higher risk zone. This may trigger additional actions, such as, but not limited to, additional cleaning or restricted access.

The video 310 may also be analyzed by a risky behaviors module 314 which may be stored in a memory 130 of the controller 102. In some cases, the social distancing module 312 and the risky behaviors module 314 may run simultaneously or one after the other. In other cases, a single module may be used to analyze the video for risky behavior. The risky behaviors module 314 may be configured to analyze how risky the movement and/or behavior of the people in the video is, whether or not the people in the video are wearing PPE, if someone sneezes or coughs, etc. More generally, the risky behaviors module 314 is configured to analyze the video to identify behavior that is more likely to increase a risk of spread of a contagion. In some cases, risky behaviors can include people violating social distancing guidance for at least a threshold dwell time, people making physical contact (e.g., shaking hand, patting a back, etc.), people not wearing face masks or other PPE around others, people sneezing or coughing, etc.

"Nearness behavior" may consider the number of times nearness is seen in the given number of frames. "Nearness" is used to describe when two or more people are less than a distance threshold apart. In some cases, "nearness" may be the average distance (in real-world units) separating two or more people during non-compliance. For example, nearness may be calculated as defined in Equation 2:

$$\text{Nearness} = \frac{\sum_{i=1}^{B} D_i}{B * \text{NormDistance}}{N}$$

Equation 2 where B is the number of people in the frame not adhering to the threshold distance, $D_i$ is the distance of each person in the frame not adhering to the norm, NormDistance is the threshold distance, and N is the total number of frames considered. As set forth above, the threshold distance may be user defined and may vary from situation to situation. In some cases, the threshold distance may be about 6 feet (about 1.8 meters).

The nearness behavior can be used to describe the frequency of nearness or non-adherence. For example, nearness behavior may be calculated as defined in Equation 3:

$$\text{NearnessBehavior} = \frac{\sum_{j=1}^{P} N_p}{P_{Total}}{N}$$

Equation 3 where $N_j$ is the number of people (P) who are not adhering to the threshold distance, $P_{Total}$ is the total number of people in the frame, and N is the total number of frames that are being processed.

A weighted average of the nearness behavior and the nearness may be used to define at least some "risky behavior". For example, the distance between two or more people is relatively less important with people at 5.5 feet (about 1.5 meters) apart than with people at 2 feet (about 0.6 meters) apart. While both may be less than the desired distance threshold of 6 feet (or about 1.8 meters), people that are two feet apart may be more likely to spread a contagion. In some cases, two or more predetermined distance thresholds are used to further differentiate risky behavior. In some examples, risky behavior may be calculated as defined in Equation 4:

$$\text{RiskyBehaviors} = a_1 * \text{NearnessBehavior} + a_2 * \text{Nearness}$$

Equation 4 where $a_1$ and $a_2$ are constants representing the weight given to each of the nearness behavior and the nearness. The constants may be adjustable depending on the situation. The risky behavior metric can include or factor in other behaviors as well. Other behaviors may include, but are not limited to, whether or not the individuals are wearing a mask or not, how long two or more individuals are below each of the predetermined distance thresholds, whether or not any of the two or more individuals sneezed or coughed, etc. The presence of other behaviors in addition to being in close proximity may increase the risky behavior metric. Skin temperature may also be used if available to help identify those people that might have a disease.

When the risky behavior score or metric, as determined in Equation 4, exceeds a predetermined threshold, a real-time alert 316 may be generated. In some cases, the alert may be an audio alert transmitted directly to the monitored space and hence the people exhibiting the risky behavior. In other cases, a real-time audio or written alert may be transmitted to a remote device. The remote device may be a part of the building management system, a mobile device of a supervisor, etc. In some cases, the alert 316 may be displayed at the video surveillance monitoring station. The alert 316 may include a location or zone of the non-compliance and/or a number of people who are non-compliant. In some cases, the alert may include a recommended action, such as, but not limited to, screening the non-compliant people for symptoms of an illness or providing a reminder of the health guidelines. In some cases, the non-compliant people may be identified through facial recognition or other techniques, and the identity of the non-compliant people may be reported.

In some cases, it may be necessary or useful to narrow down a risky area to a particular area or sub-zone. This may be used to help enforce social distancing in a public building or space where an authority (e.g., a security guard) may be brought in to enforce social distancing. This is just one example. Alternatively or additionally, regions or minimum bounding rectangles (MBRs) may be drawn around of each person of those who are less than the threshold distance apart. A minimum bounding rectangle may be a box that is drawn around people detected in the scene (using, for example, video analytics). This may be performed for each frame (e.g. N frames) where two or more people are less than the threshold distance apart. The MBRs across the N frames may be aggregated and the risky behavior score (e.g., RiskyBehaviors from Equation 4) determined. The MBRs may then be used to determine a high risk sub-zone of an area.

Figure 5:
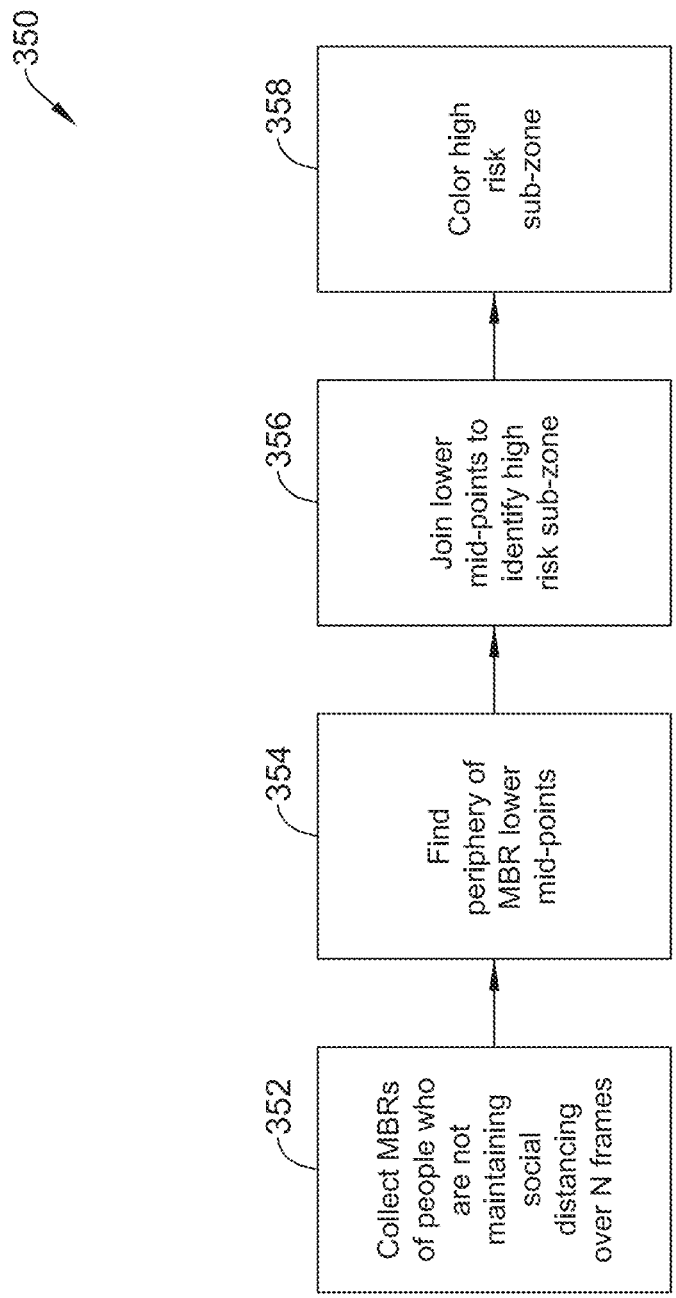
FIG. 5A is a flow chart of an illustrative method for identifying and displaying higher risk sub-zones of a building or other space.
FIG. 5B is a schematic representation of the method of FIG. 5A.

Reference will now be made to both to FIG. 5A which is a flow chart of an illustrative method 350 for identifying and displaying high risk sub-zones and FIG. 5B which is a schematic representation 380 of the method 350 of FIG. 5A. The method 350 may be performed by the controller 102 or video analytics within the video camera 108 or on a video analytics server. To begin, the MBRs of people who are less than the threshold distance apart (e.g., not maintaining social distancing) may be collected over N frames, as shown at block 352. FIG. 5A illustrates a first person 360a at a first location (e.g., a first frame) and a second person 362a at a first location (e.g., the same first frame). In the first frame, the first person 360a and the second person 362a are a first distance D1 apart. D1 is determined to be less than the minimum threshold distance for maintaining social distancing. An MBR 364a is drawn around the first person 360a in the first frame and an MBR 364b is drawn around the second person 362a in the first frame. FIG. 5B also illustrates the same two people 360b, 362b in an Nth frame corresponding to a different or possibly a same location as the first frame. In the Nth frame, the first person 360*b* and the second person 362*b* are a second distance D2 apart. D2 is determined to be less than the minimum threshold distance for maintaining social distancing. An MBR 364*c* is drawn around the first person 360*b* in the Nth frame and an MBR 364*d* is drawn around the second person 362*b* in the Nth frame. In some cases, the Nth frame may be the last frame where two or more people were at less than the minimum threshold distance, although this is not required.

Next, the periphery MBR lower mid-points 366*a*, 366*b*, 366*c*, 366*d* (collectively, 366) may be found in each row of the image to define perimeter points, as shown at block 354. The lower mid-points of the MBR are the middle of the bottom edge of the rectangle and generally correspond to the middle of the feet of the person. If there are repeated violations of social distancing in a particular sub-region, the lower MBR mid-points 366 for N number of frames are used to draw one or more polygons. For example, the lower MBR mid-points 366 may be joined in each row of the image to define perimeter points forming a polygon 368 to identify the high risk sub-zone (e.g., the space within the polygon) 370, as shown at block 356. The high risk zone 370 may be shaded a different color or made transparent to visually indicate the zone, as shown at block 358. It is contemplated that an image of the space including the high risk sub-zone may be transmitted to a remote device. The remote device may be a part of the building management system, a mobile device of a supervisor, etc. In the illustrative embodiment of FIG. 5B only four lower MBR mid-points 366 have been joined to form the polygon 368. However, it should be noted that any number of lower MBR mid-points 366 may be joined. The number of lower MBR mid-points 366 may be based on the number of people violating the social distancing guidelines and the number of frames over which the violations occurred.

Figure 6:
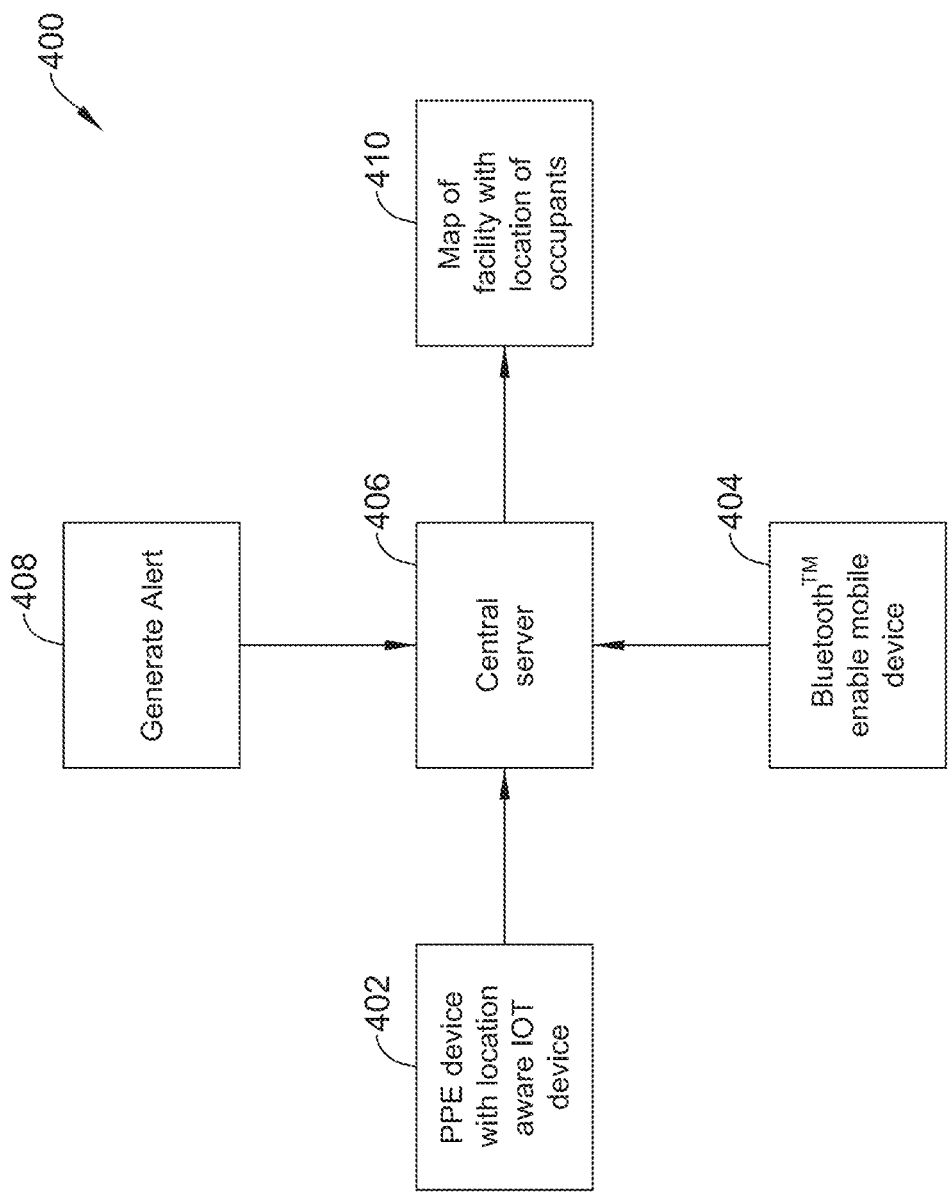
FIG. 6 is a block diagram of an illustrative people tracking system.

In some cases, video cameras and hence their video streams may not be available to determine if people are maintaining at least a threshold distance between themselves and others. Yet, it may still be desirable to determine if people are staying at least a predetermined threshold distance from other people (e.g., about 6 feet or 1.8 meters, although this may vary), if people are gathering in groups, and/or if people are staying out of crowded places even when video surveillance is not available or practical. FIG. 6 is a block diagram of an illustrative people tracking system 400. The system 400 may be configured to receive location information from location aware devices. In some cases, an article of personal protective equipment (PPE) may be fitted with a location aware internet of things (JOT) device 402. The type of PPE may vary depending on the environment. For example, PPE in a manufacturing facility or construction environment may include, but is not limited to, safety glasses, hearing protection, hand protection, foot protection, hard hats, etc. PPE in health care environment may include, but is not limited to, face masks, gloves, face shields, protective clothing, etc. It is contemplated that the location aware IOT device 402 may be coupled to, embedded in, or otherwise affixed to the PPE. In some cases, the IOT device 402 may linked to a specific person, although this is not required. For example, the location aware IOT device 402 may capable of providing an identity of the person wearing the PPE as well as the location of the person.

The IOT device 402 may be configured to transmit the location of the PPE (and thus the presumed location of a person) to a central server 406. The server 406 may be a remote or cloud based server or may be local to the building, as desired. In some cases, it is contemplated that the IOT device 402 may be in communication with the server 406 over a local area network (LAN), a wide area network or global network (WAN) including, for example, the Internet, wireless 4/5G, LTE, etc.

Alternatively, or in addition, the IOT device 402 may provide a signal that is received by one or more of a plurality of location beacons (e.g. Bluetooth Low Energy) distributed about a region of interest. A location of the IOT device 402 may be identified From the signals received by the one or more of the plurality of beacons. Any other suitable location service may be used to identify the location of the IOT device 402. In some cases, the IOT devices 402 may provide GPS coordinates for a more precise distance determination.

In any case, the location may be sent to the central server 406. The server 406 may be configured to determine a distance between two or more IOT devices 402

In some cases, such as for example, an office environment, PPE may not be mandatory. In such an instance, Bluetooth™ enabled mobile phones 404, or other Bluetooth™ enabled devices may be used to track the location of people. For example, the mobile device 404 may be configured to determine a distance between it and another Bluetooth™ enabled device. In some cases, a software application (or app) may be installed on the mobile device 404. The app may include the control logic to search for other Bluetooth™ signals and to determine a distance between the current mobile device 404 and the other mobile device emitting the Bluetooth™ signal. It is contemplated that other short range communication protocols may be used as desired. The mobile device 404 may transmit the distance between itself and other Bluetooth™ device to the central server 406.

The central server 406 may compare the distance between IOT devices 402 and the distance between mobile devices 404. If the distance between any two IOT devices 402 and/or the distance between any two mobile devices 404 is less than a threshold distance, the central server may determine that the IOT devices 402 and/or the mobile devices 404 are too close together and the people associated with these devices 402, 404 are not adhering to social distancing guidelines. The server 406 may then generate an alert 408. In some cases, the alert 408 may be sent to the non-compliant users (if the identity is known). Alternatively or additionally, the alert 408 may be sent to a building management system, a health office, a supervisor, etc. The alert 408 may be an audio alert including, but not limited to, a recorded voice message or a tone, beep, ringer delivered to a nearby speaker, a mobile device, a walkie-talkie, etc. The alert 408 may be a haptic alert delivered to a mobile device. In some cases, the alert may be a textual or natural language written message transmitted to a mobile device (e.g., SMS or e-mail). Generally, the alert 408 may indicate the non-compliance, a location of the non-compliance, and/or the identity of the occupants involved.

The central server 406 may be further configured to display the location of the occupants on a map of the facility 410. It is contemplated that the map 410 may be continually displayed and updated, for example, at a central monitoring station for real time visual monitoring of social distancing compliance. In some cases, the map 410 may be displayed in response to a user request. For example, a user may submit a request (e.g., via an app or internet based portal) to the server 406. In response, the server 406 may transmit the real time map with occupant location 410 to the requesting device. In some cases, a user may view the map 410 to determine if they can safely enter a particular area or if the area appears to be crowded.

If the server 406 has detected that any two people in a particular area or zone of the facility are not maintaining social distancing, the server 406 may be configured to shade the particular area a different color, such as, but not limited to, red to readily draw the user's attention to the non-compliant. It is contemplated that if a particular area stays in non-compliance for greater than a threshold period of time and/or if a number of people involved in the non-compliance exceeds a threshold number an alert may be generated for an authority (e.g., security, health team, etc.) to take appropriate action. Action may include asking the occupants to disperse, providing additional training, providing health screenings for those involved, etc.

It is further contemplated that the location of people within a building or facility can allow others to base their movements on the location of others. For example, in an office environment, an occupant may wish to visit a common area such as, but not limited to, a coffee station, a breakroom, a copy room, a conference room, etc. However, prior to leaving their workstation, the occupant has no way of knowing if the common area is occupied and/or if the occupancy exceeds a predetermined maximum number. The predetermined maximum number may be the number of people that can occupy a space while maintaining a minimum threshold distance between each of the people.

Figure 7:
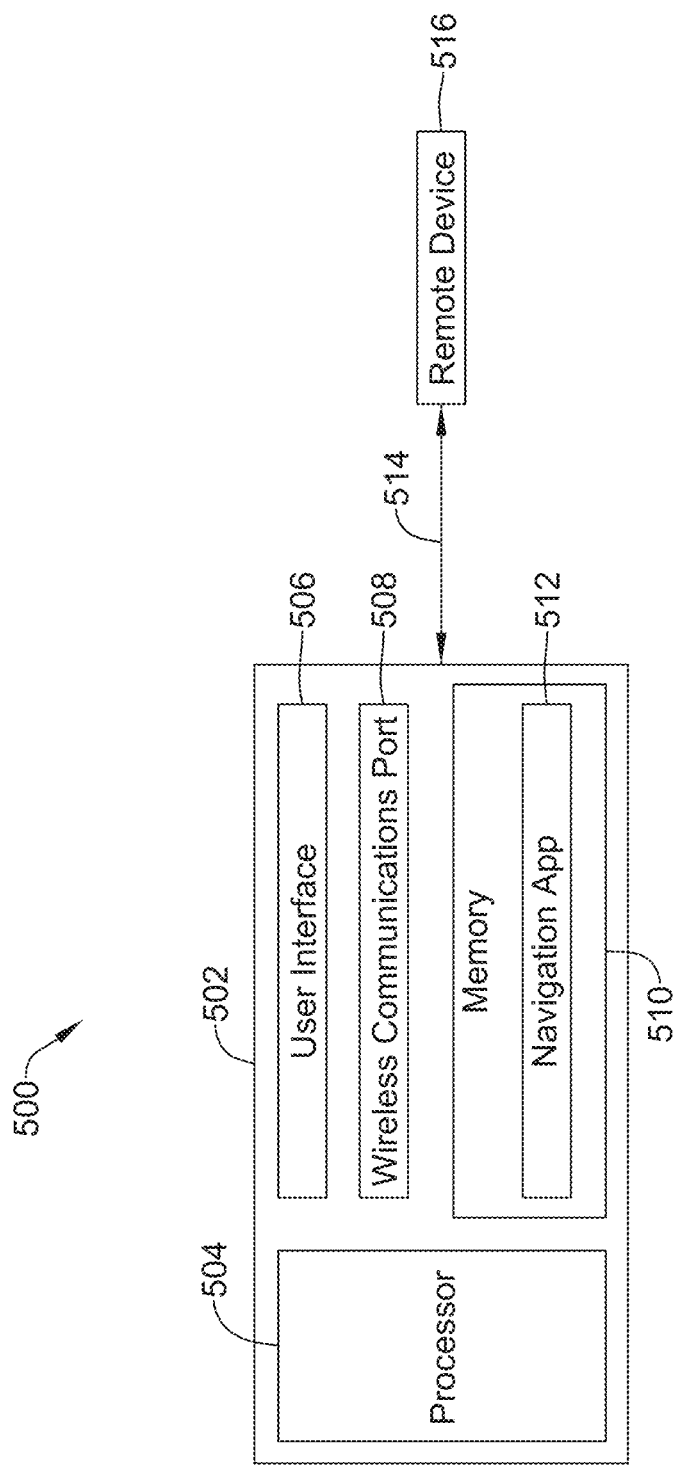
FIG. 7 is a schematic block diagram of an illustrative mobile indoor navigation system.

FIG. 7 is a schematic block diagram of an illustrative mobile indoor navigation system 500 that may facilitate maintaining a predetermined threshold distance between two or more people. The system 500 may include a mobile device 502, such as, but not limited to a smartphone or tablet computer. The mobile device 502 may include a processor 504 (e.g., microprocessor, microcontroller, etc.) and a memory 510. The mobile device 502 may further include a user interface 506 including a display and a means for receiving user input (e.g., touch screens, buttons, keyboards, etc.). The memory 510 may be in communication with the processor 504. The memory 510 may be used to store any desired information such as, but not limited to, control algorithms, software applications, acquired images, event logs, etc. The memory 510 may be any suitable type of storage device including, but not limited to, RAM, ROM, EPROM, flash memory, a hard drive, and/or the like. In some cases, the processor 504 may store information within the memory 510, and may subsequently retrieve the stored information from the memory 510.

The mobile device 502 may further include a wireless communication port 508 including a wireless transceiver for sending and/or receiving signals over a wireless network 514. The network 514 may be including a local area network (LAN) or a wide area network or global network (WAN) including, for example, the Internet, wireless 4/5G, LTE, etc. The mobile device 502 may communicate over the network 514 with a remote device 516. In some cases, the remote device 516 may be another mobile device, a cloud based server, a BMS server, a video management server (VMS) etc. The remote device 516 may include a controller, a processor, a memory, wireless communication means, etc. It is contemplated that the mobile device 502 may be pre-registered with the remote device 516 to allow secure communication therewith. For example, the mobile device 502 may be registered with the remote device 516 using the International Mobile Equipment Identity (IMEI) number of the mobile device 502, Bluetooth™ communication, a mobile telephone number of the mobile device 502, a mobile hotspot, etc.

The remote device 516 is configured to receive and/or determine the location of occupants of a building, facility, space, etc. For example, the remote device 516 may use video analytics and people recognition techniques to determine the location of people in a similar manner as described with respect to FIGS. 2 and 3. Alternatively or additionally, the remote device 516 may receive location information from location enabled TOT device or mobile devices, such those described with respect to FIG. 6. The remote device 516 may be further configured to overlay the location of the occupants on a facility map and/or to maintain a database of the locations. The location of the occupants on a facility map and/or the database may be continually updated in real time so that occupancy data is up-to-date.

The mobile device 502 may be a mobile device 502 carried by an occupant of the building. The occupant may download a navigation application (app) 512 to be stored in the memory 510 thereof and executed by the processor 504. Generally, the application 512 may be configured to use occupant location data from the remote device 516 to determine if a person can safely (e.g., by limiting contact with others) travel to and/or occupy a common area. While the system 500 is illustrated as including a single mobile device 502, it should be noted that the system 500 may utilize any number of mobile devices 502. For example, each occupant or user of the building may possess their own unique mobile device 502 that is in communication with the remote device 516.

Figure 8:
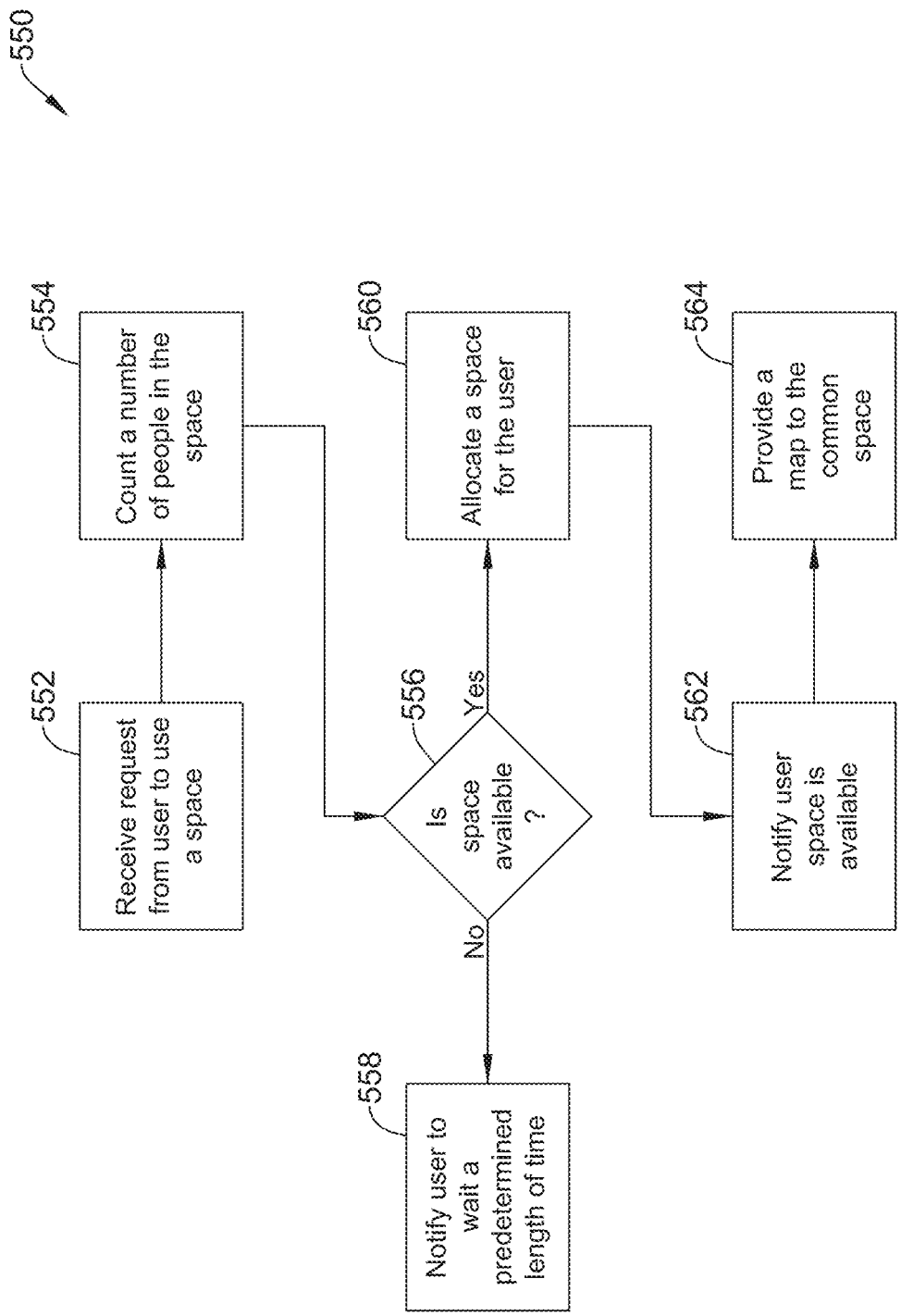
FIG. 8 is a flow chart of an illustrative method for reducing a risk of spread of an illness in a building by providing a reservation system for a space.

FIG. 8 is a flow chart of an illustrative method 550 for reducing a risk of spread of an illness in a building by providing up-to-date occupant location to one or more users via the application 512 on a user's mobile device 502. When a user wishes to visit a common area of a building, the user may open the navigation app 512 on their mobile device 502. The user may then use the application to submit a request to visit a particular common area or space of the building. The remote device 516 may receive the request from the user, as shown at block 552. The remote device 516 may then count a number of people present in the common area the user wishes to access, as shown at block 554. As noted above, the remote device 516 may use video analytics and people recognition techniques to determine the location of people in a similar manner as described with respect to FIGS. 2 and 3. Alternatively or additionally, the remote device 516 may receive location information from location enabled IOT device or mobile devices, such as the mobile device 502 requesting information, such those described with respect to FIG. 6. In some cases, the remote device 516 may be configured to count people who have reserved a space in the common area as present when determining a people count, as will be described in more detail herein.

The remote device 516 may then compare a number of people in the space to a threshold number (e.g., a maximum allowable number of people for the space) to determine if space is available for the requesting user, as shown at block 556. If the number of people in the requested common area is less than the threshold number, the remote device 516 determines that space is available for the requesting user. The remote device 516 may allocate a virtual space for the user in the requested common space, as shown at block 560. For example, the remote device 516 may consider the user to have placed a reservation for use of the common area and increased the people count to include the requesting user that will be traveling to the common area. This may help prevent overcrowding of the common area when additional users request to the use the same common space before the previous requesting user has arrived in the space. In some cases, the allocation of the virtual space may be associated with a predetermined length of time for the user to occupy the common area. It is contemplated that this may allow the remote device 516 to generate a queue and/or an estimated wait time if multiple people wish to use the common space at a similar time.

The remote device 516 may then transmit a notification to the user for display on the mobile device 502 indicating that space is available and the user may travel to the common area, as shown at block 562. In some cases, the notification may indicate to the user a length of time they may use the common area or a time by which they should exit the common space. The remote device 516 may also provide or transmit a map to the mobile device 502, as shown at block 564. The map may include a route from a current location of the user (e.g., based on a location of the mobile device 502 as determined using GPS and/or Bluetooth™) to the common area. The remote device 516 may determine a route that minimize interaction of the requesting user with other users or building occupants. It is further contemplated that the route may be updated (e.g., changed) in real time as the user moves to the common area, for example, if a better route becomes available that further minimizes interaction with other people. In some cases, if a safe route is unavailable, the requesting user may be asked to wait in their current place until they receive notification that a safe route is available. In addition to displaying a route, the map may also display the location of the current user and/or other users in the building.

If space is not available in the requested common area (e.g., the number of people in the common area and/or traveling to the common area is equal to or greater than the threshold number of allowable people), the remote device 516 may transmit a notification to the user for display on the mobile device 502 indicating that the requested common space is currently unavailable and the user should wait a predetermined length of waiting time before traveling to the requested common area or making another request, as shown at block 564. The predetermined length of time may be determined, at least in part, by a number of other users in queue to use the common area. In some cases, the notification may indicate to the user to resubmit the request after a predetermined length of time to verify that a space has indeed become available. In some cases, when space is not available, the remote device 516 may transmit an alert to the current occupants of the requested space that there are other users waiting to use the space. In some cases, the alert may be delivered via the application 512. In other cases, the alert may be in SMS or e-mail format. It is further contemplated that the alert may be an audio alert delivered via a speaker in the common area.

In some cases, artificial intelligence may be used to learn the movement patters of the occupants over time. For example, the system may learn from past data that the break room becomes crowded at 8:30 AM-9:30 AM, 11:00 AM-1:00 PM and 3:30-4:00 PM each day. This can be used to provide a better estimate of when a space may open up for the requesting user.

In addition to limiting the number of people present in a common space, it may be desirable to space the people such that a predetermined distance threshold is maintained between each person. For example, in a conference room, it may be desirable to space chairs a predetermined distances apart. However, to optimize efficient use of time and space, it is desirable to maximize the occupancy of a space while ensuring social distancing guidelines are followed. It is contemplated that security cameras or other installed still image or video cameras may be utilized to help determine and accommodate a maximum number of people in a space while still complying with social distancing protocols (e.g., maintain a minimum predetermined distance between each person).

Figure 9:
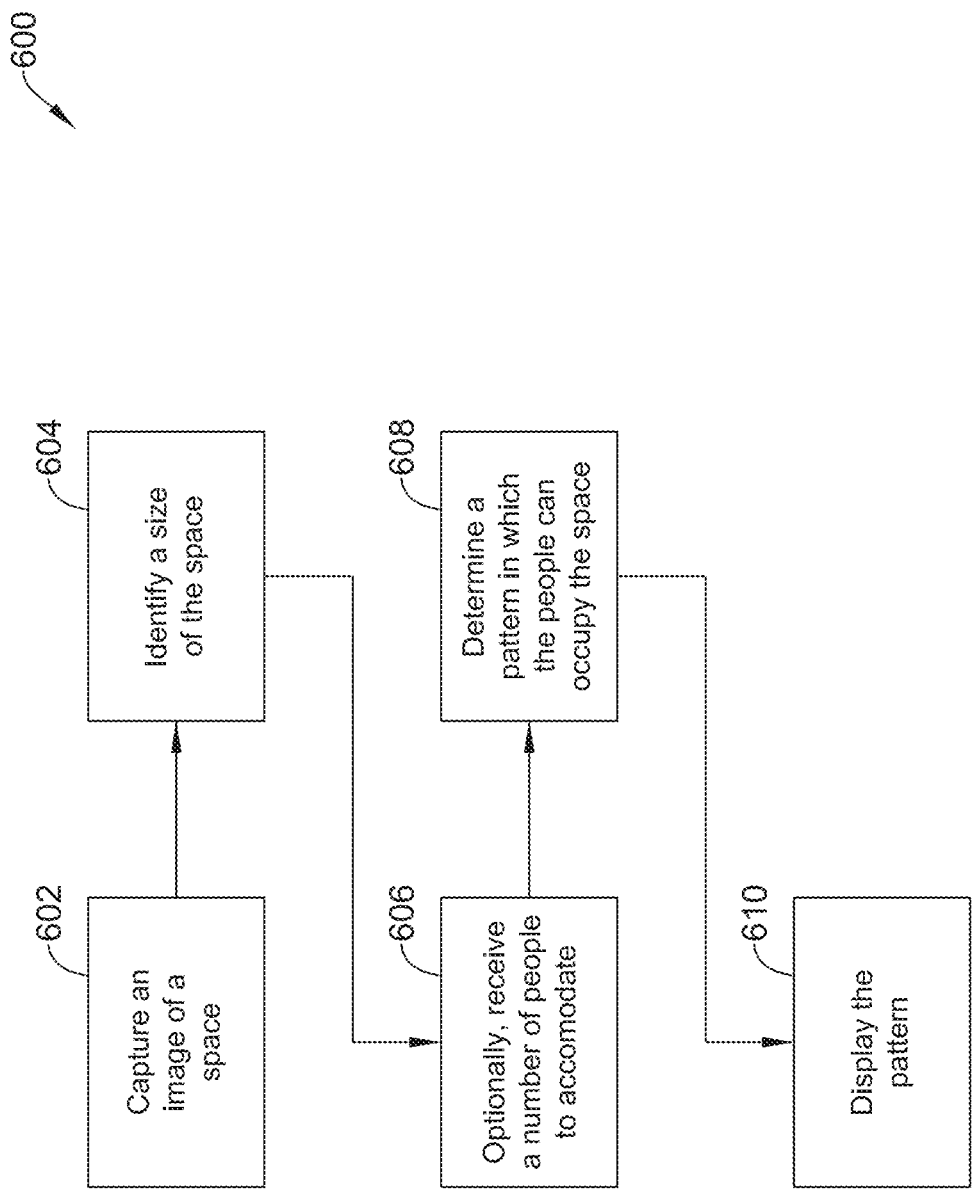
FIG. 9 is a flow chart of an illustrative method for determining an arrangement of a group of people in a space.

FIG. 9 is a flow chart of an illustrative method 600 for determining an arrangement of a group of people in a space. First an image of the space may be captured, as shown at block 602. It is contemplated that the image may be acquired using a video camera, such as, but not limited to, the video cameras 108 described herein. It is contemplated that the image may be acquired in response to a user input. In some cases, the image may be captured by a mobile phone and/or tablet computer.

Once the image has been captured, the size of the space may be determined or identified, as shown at block 604. It is contemplated that the size of the space may be determined using video analytics as described with respect to FIG. 4. In other cases, the size of the space may be retrieved from a building floor plan or model. In some embodiments, the user may input the number of people to be accommodated, as shown at block 606. In other cases, the processor may determine the arrangement based on a determined maximum number of people that can be accommodated. In other case, the system may count the number of people currently in the space, in a manner as described above. In any event, the processor may determine a pattern in which the group of people can occupy the space while maintaining a predetermined distance between each person, as shown at block 608.

The processor may include a self-learning algorithm which utilizes the predetermined distance required between people to determine and recommend a pattern and/or arrangement in which the people should sit or stand in order to maintain social distance. It is contemplated that the predetermined distance may be a user defined and modifiable variable. For example, the predetermined distance may be at least 6 feet (about 1.8 meters) during times of a pandemic. The predetermined distance may be less than 6 feet (about 1.8 meters) at other times, as desired. It is contemplated that the processor may be configured to consider inputs or factors other than just spacing when determining the recommended pattern. For example, if a speaker is to be present, the processor may apply a rule that indicates the occupants should be arranged to face a same direction (e.g., in a linear pattern). If small group conversations are to occur, the processor may apply a rule to arrange small groups of people to face one another (e.g., in a square or circular pattern). These are just some examples. Other rules may be applied as appropriate. It is further contemplated that the pattern may be dynamically updated to recommend the best pattern as the total number of people increase and/or decrease in a space. For example, a people counter, such as the one described herein, may continually update the processor with a current number of people in the room. The processor may then continually update the pattern. If there is no pattern that will allow the number of people in the group of people to occupy the space while maintaining the predetermined distance between each person, the processor may generate and/or transmit an alert. The alert may be an audio alert, a textual alert, a haptic alert, etc. transmitted to a supervising user.

Figure 10:
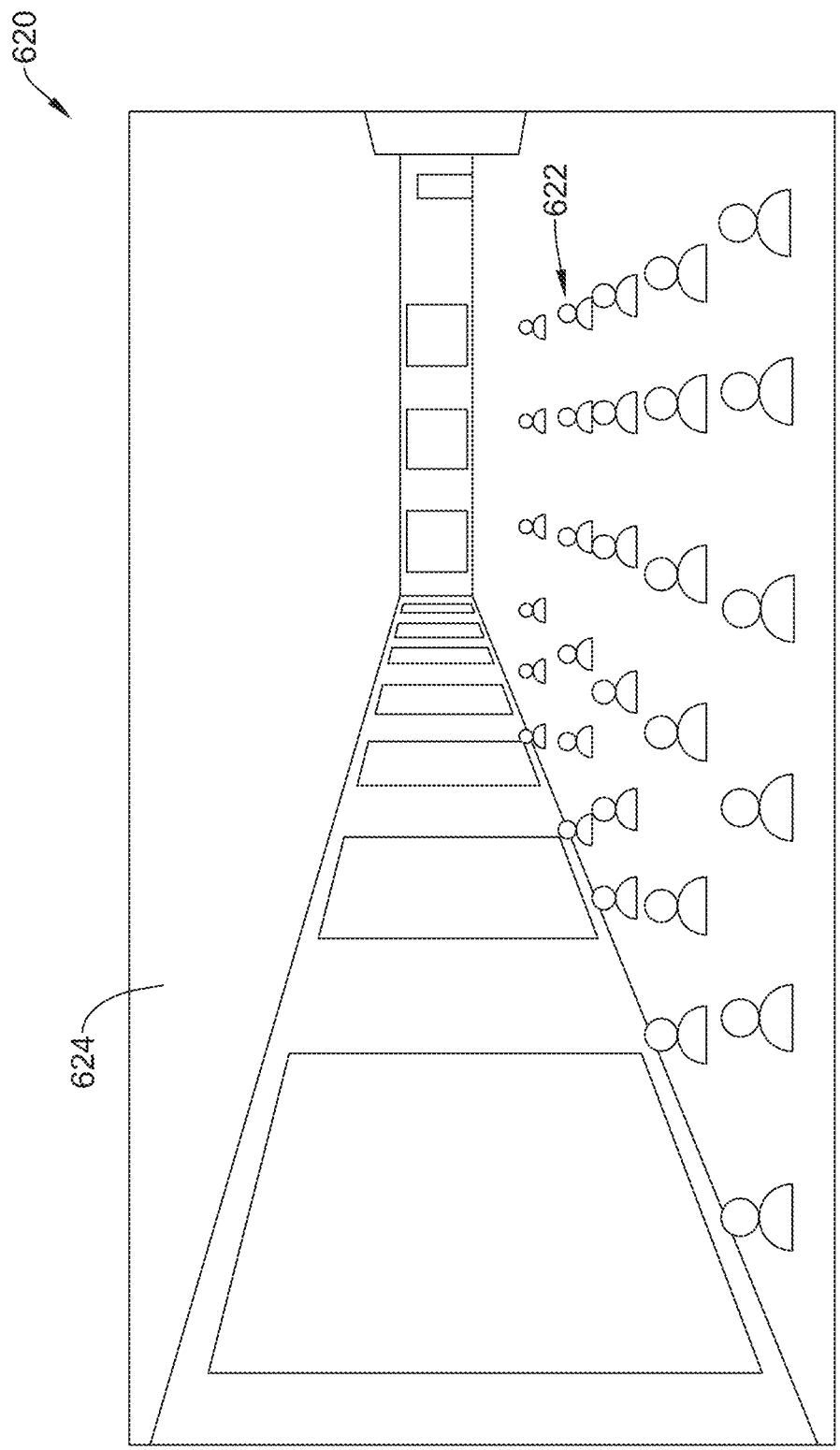
FIG. 10 is a schematic view of an illustrative display having a generated pattern of people placement overlaid on an image of a space.

The processor may be further configured to display the recommended pattern on a user interface (for example, if performed remote from the video camera) or a remote device (for example, if performed at the video camera), as shown at block 610. The pattern may be displayed over the acquired image as shown in FIG. 10 illustrates a schematic view of an illustrative display 620 having a pattern 622 of overlaid on an image 624 of space. The pattern may include both or one of a representation of people and furniture in the space (or to be positioned in the space). In some cases, the image may be displayed at a control center for a video management server (VMS). In other cases, the image may be transmitted to a remote device or a mobile device. It is contemplated that in some cases, a building supervisor or other authorized user may input variables and/or initiate the pattern development via the VMS. This may allow the user to initiate or develop a plurality of pattern determinations on a plurality of different spaces from a central location. The VMS may be configured to allow a user to move between user selectable options, including viewing of the video camera feeds, configuration of the occupant patterns in the field of view of cameras, etc. The VMS may further be configured to display information such as a maximum number of people the space can accommodate based on differing predetermined distance thresholds. In some cases, the building supervisor or other occupant may prearrange chairs or mark floors with tape to identify where people or furniture should be located based on the displayed pattern.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A method for counting a number of people in a space of a building, the method comprising:
   storing a background image of a perspective field of view captured by a non-overhead video camera;
   receiving a video stream from the non-overhead video camera;
   calibrating the perspective field of view captured by the non-overhead video camera, including:
      determining a number of pixels of the non-overhead video camera that correspond to a known-sized object at a known location at a near end of the perspective field of view of the non-overhead video camera, and a number of pixels of the non-overhead video camera that correspond to a known-sized object at a known location at a far end of the perspective field of view of the non-overhead video camera;
      generating a calibration map that maps real world distances in the perspective field of view of the non-overhead video camera against x-and y-pixel positions of the non-overhead video camera based at least in part on the number of pixels of the non-overhead video camera that correspond to the known-sized object at the known location at the near end of the perspective field of view of the non-overhead video camera and the number of pixels of the non-overhead video camera that correspond to the known-sized object at the known location at the far end of the perspective field of view of the non-overhead video camera;
   subtracting the background image from each frame of the video stream to identify one or more blobs in the perspective field of view of the non-overhead video camera;
   determining a real-world distance between the non-overhead video camera and each of the one or more blobs based at least in part on the calibration map;
   comparing a size of each of the one or more blobs to an expected size of a person at the determined distance of the corresponding blob;
   when the size of the blob is greater than the expected size of a person at the determined distance of the corresponding blob by more than a factor of at least 1.5 times, counting the blob as two or more people, otherwise counting the blob as one person or no person; and
   determining a count of the number people in the perspective field of view of the non-overhead video camera based at least in part on the count of people assigned to each of the one or more blobs.

2. The method of claim 1, wherein when the size of the blob is not greater than at least 1.5 times the expected size of a person at the determined distance, using deep learning to determine whether to count the blob as one person or no person.

3. The method of claim 2, wherein the perspective field of view of the non-overhead video camera covers only part of the space of the building, and wherein a perspective field of view of one or more other non-overhead video cameras cover one or more other parts of the space, the method further comprising:
   determining a count of the number people in the perspective field of view of each of the one or more other non-overhead video cameras; and
   aggregating the counts of the number of people from all of the non-overhead video cameras that have a perspective field of view that covers part of the space to identify a total count of the number of people in the space.

4. The method of claim 3, further comprising updating the total count of the number of people in the space at predetermined time intervals to obtain a plurality of total counts over a period of time.

5. The method of claim 4, further comprising determining a rate of change of the total count of the number of people in the space.

6. The method of claim 5, further comprising displaying a map of the one or more spaces of the building and shading each of the one or more spaces of the map based on the determined rate of change the total count of the number of people in the corresponding space.

7. A method for counting a number of people in a space of a building, the method comprising:
   storing a background image of a field of view of each of two or more video cameras;
   calibrating a field of view of each of the two or more video cameras, where for each of the two or more video cameras:
      determining a number of pixels of the respective video camera that correspond to a known-sized object at a known location at a near end of the field of view of the respective video camera, and a number of pixels of the respective video camera that correspond to a known-sized object at a known location at a far end of the field of view of the respective video camera;
      generating a calibration map that maps real world distances in the field of view of the respective video camera based at least in part on the number of pixels of the respective video camera that correspond to the known-sized object at the known location at the near end of the field of view of the respective video camera and the number of pixels of the respective video camera that correspond to the known-sized object at the known location at the far end of the field of view of the respective video camera;

receiving a video stream from each of the two or more video cameras;

subtracting the background image from one or more frames of the respective video stream to identify one or more blobs in the respective field of view of each of the two or more video cameras;

determining a distance between the respective video camera of the two or more video cameras and each of the one or more blobs that are associated with the respective video camera based at least in part on the corresponding calibration map;

comparing a size of each of the one or more blobs to an expected size of a person at the determined distance of the corresponding blob;

when the size of the blob is greater than the expected size of a person at the determined distance of the corresponding blob by more than a predetermined factor that is greater than one, counting the blob as two or more people, otherwise counting the blob as one person or no person; and determining a count of the number people in the respective field of view of each of the two or more video cameras; and aggregating the counts of the number of people from all of the video cameras that have a field of view that covers part of the space to identify a total count of the number of people in the space.

8. The method of claim 7, further comprising updating the total count of the number of people in the space at predetermined time intervals to obtain a plurality of total counts over a period of time.

9. The method of claim 8, further comprising determining a rate of change of the total count of the number of people in the space.

10. The method of claim 9, further comprising displaying a map of the one or more spaces of the building and shading each of the one or more spaces of the map based on the determined rate of change the total count of the number of people in the corresponding space.

* * * * *